US007855050B2

(12) United States Patent
Ouwehand et al.

(10) Patent No.: US 7,855,050 B2
(45) Date of Patent: Dec. 21, 2010

(54) DIAGNOSIS OF ABNORMAL BLOOD CONDITIONS BASED ON POLYMORPHISMS IN THE GLYCOPROTEIN VI GENE

(76) Inventors: Willem Ouwehand, Department of Haematology, University of Cambridge, Long Road, Cambridge (GB) CB2 2PT; Peter Alexander Smethurst, 118 Pheasant Rise, Bar Hill, Cambridge (GB) CB3 8SD; Richard Willam Farndale, 21 Hawthorne Road, Stapleford, Cambridge (GB) CB2 5DU ( * ) Notice: Subject to any disclaimer, the term of this patent is extended or adjusted under 35 U.S.C. 154(b) by 582 days.

(21) Appl. No.: 10/514,999

(22) PCT Filed: May 22, 2003

(86) PCT No.: PCT/GB03/02208

§ 371 (c)(1), (2), (4) Date: Jun. 24, 2005

(87) PCT Pub. No.: WO03/097875

PCT Pub. Date: Nov. 27, 2003

(65) Prior Publication Data

US 2005/0255470 A1 Nov. 17, 2005

(30) Foreign Application Priority Data

May 22, 2002 (GB) ................................. 0211750.5

(51) Int. Cl.
*C12Q 1/68* (2006.01)
*C07H 21/04* (2006.01)
*C12P 19/34* (2006.01)
(52) U.S. Cl. .......................... 435/6; 536/24.3; 536/23.1; 435/91.2
(58) Field of Classification Search ....................... None
See application file for complete search history.

(56) References Cited

U.S. PATENT DOCUMENTS

| 6,383,779 B1 | 5/2002 | Busfield et al. ............. 435/69.1 |
| 6,825,323 B2 * | 11/2004 | Hess ............................ 530/384 |
| 2003/0186244 A1 * | 10/2003 | Margus et al. .................. 435/6 |

FOREIGN PATENT DOCUMENTS

| WO | WO 99/50281 | 10/1999 |
| WO | WO 01/16321 | * 3/2001 |

OTHER PUBLICATIONS

Risch, Neil. Searching for genetic determinants in the new millennium. 2000. Nature. vol. 405, pp. 847-856.*
Heid, CA et al. Real time quantitative PCR. 1996. Genome Research. vol. 6, pp. 986-994.*
Rebulla, P. Platelet transfusion trigger in difficult patients. 2001. Transfusion Clinical Biology. vol. 8, p. 249-254.*
Tabor, Holly et al. Candidate gene approaches for studying complex genetic traits: practical considerations. Nature Reviews Genetics. 2002 vol. 3 pp. 1-7.*
Wacholder, Sholom et al. Assessing the probability that a positive report is false: an approach for molecular epidemiology studies. Journal of the National Cancer Institute. 2004. vol. 96 pp. 434-442.*
Suzuki-Inoue, Katsue et al. Assoication of Fyn and Lyn with the proline rich domain of glycoprotein VI regulates intracellular signaling. 2002. The Journal of Biological Chemistry. vol. 277 No. 24 pp. 21561-21566.*
Cole, VJ et al. Collagen platlet receptor polymorphism integrin a2B1 C807T and GPVI Q317L and risk of ischemic stroke. 2003. Journal of Thrombosis and Haemostasis. vol. 1 pp. 963-970.*
Croft, S., et al., "Novel Platelet Membrane Glycoprotein VI Dimorphism is a Risk Factor for Myocardial Infarction," *Circulation*, 104(13):1459-63, Sep. 25, 2001.
Croft, S., et al., "The GPIa C807T Dimorphism Associated with Platelet Collagen Receptor Density is Not a Risk Factor for Myocardial Infarction," *Br. J. Haematol.*, 106(3):771-6, Sep. 1999.
Furihata, K., et al., "Variation in Human Platelet Glycoprotein VI Content Modulates Glycoprotein VI-specific Prothrombinase Activity," *Arterioscler Thromb. Vasc. Biol.*, 21(11):1857-63, Nov. 2001.
Griffin, H., et al., "A Human Monoclonal Antibody Specific for the Leucine-33 (P1A1, HPA-1a) form of Platelet Glycoprotein IIIa from a V Gene Phage Display Library," *Blood*, 86(12):4430-6, Dec. 15, 1995.
Joutsi-Korhonen, L., et al., "The Low-frequency Allele of the Platelet Collagen Signaling Receptor Glycoprotein VI is Associated with Reduced Functional Responses and Expression," *Blood*, 101(11):4372-9, Jun. 1, 2003. Epub Jan. 30, 2003.
Kunicki, T., et al., "The Influence of Platelet Collagen Receptor Polymorphisms in Hemostasis and Thrombotic Disease," *Arterioscler Thromb Vasc Biol.*, 22(1):14-20, Jan. 2002.
Ouwehand, W., "Figures 1, 2, 4a, 4c, 5, and 6 of Patent Application: GPVI Polymorphism and Platelet Function," disclosed in a closed workshop meeting, May 22, 2002, 8 pages.

* cited by examiner

*Primary Examiner*—Stephen Kapushoc
*Assistant Examiner*—Amanda Shaw
(74) *Attorney, Agent, or Firm*—Seed IP Law Group PLLC

(57) ABSTRACT

Methods of diagnosis of abnormal blood conditions associated with an increased risk of bleeding are described. Subjects homozygous or heterozygous for the GPVI$^b$ allele are at considered to be at increased risk of bleeding. Kits for carrying out the methods of diagnosis, and use of the methods and kits for determining the GPVI allelotype of subjects in need of surgery, with a low platelet count, with an acquired bleeding disorder, on blood thinning drugs, or of blood donors is also described.

19 Claims, 15 Drawing Sheets

Figure 7A

```
           10        20        30        40
      ATGTCTCCATCCCCGACCGCCCTCTTCTGTCTTGGGCTGTGTCTGGGG
      TACAGAGGTAGGGGCTGGCGGGAGAAGACAGAACCCGACACAGACCCC
       M   S   P   S   P   T   A   L   F   C   L   G   L   C   L   G>
      _____GLYCOPROTEIN VI_____>
      _____SIGNAL PEPTIDE_____>

50        60        70        80        90
      CGTGTGCCAGCGCAGAGTGGACCGCTCCCCAAGCCCTCCCTCCAGGCT
      GCACACGGTCGCGTCTCACCTGGCGAGGGGTTCGGGAGGGAGGTCCGA
       R   V   P   A   Q   S   G   P   L   P   K   P   S   L   Q   A>
      _____GLYCOPROTEIN VI_____>
      _____>
                                                  _____>

100       110       120       130       140
      CTGCCCAGCTCCCTGGTGCCCCTGGAGAAGCCAGTGACCCTCCGGTGC
      GACGGGTCGAGGGACCACGGGGACCTCTTCGGTCACTGGGAGGCCACG
       L   P   S   S   L   V   P   L   E   K   P   V   T   L   R   C>
      _____GLYCOPROTEIN VI_____>
      _____DOMAIN 1_____>

150       160       170       180       190
      CAGGGACCTCCGGGCGTGGACCTGTACCGCCTGGAGAAGCTGAGTTCC
      GTCCCTGGAGGCCCGCACCTGGACATGGCGGACCTCTTCGACTCAAGG
       Q   G   P   P   G   V   D   L   Y   R   L   E   K   L   S   S>
      _____GLYCOPROTEIN VI_____>
      _____DOMAIN 1_____>

200       210       220       230       240
      AGCAGGTACCAGGATCAGGCAGTCCTCTTCATCCCGGCCATGAAGAGA
      TCGTCCATGGTCCTAGTCCGTCAGGAGAAGTAGGGCCGGTACTTCTCT
       S   R   Y   Q   D   Q   A   V   L   F   I   P   A   M   K   R>
      _____GLYCOPROTEIN VI_____>
      _____DOMAIN 1_____>

250       260       270       280
      AGTCTGGCTGGACGCTACCGCTGCTCCTACCAGAACGGAAGCCTCTGG
      TCAGACCGACCTGCGATGGCGACGAGGATGGTCTTGCCTTCGGAGACC
       S   L   A   G   R   Y   R   C   S   Y   Q   N   G   S   L   W>
      _____GLYCOPROTEIN VI_____>
      _____DOMAIN 1_____>

>C307G
                        |
          290       300 |310       320       330
      TCCCTGCCCAGCGACCAGCTGGAGCTCGTTGCCACGGGAGTTTTTGCC
      AGGGACGGGTCGCTGGTCGACCTCGAGCAACGGTGCCCTCAAAAACGG
       S   L   P   S   D   Q   L   E   L   V   A   T   G   V   F   A>
      _____GLYCOPROTEIN VI_____>
      _____DOMAIN 1_____>

340       350       360       370       380
      AAACCCTCGCTCTCAGCCCAGCCCGGCCCGGCGGTGTCGTCAGGAGGG
      TTTGGGAGCGAGAGTCGGGTCGGGCCGGGCCGCCACAGCAGTCCTCCC
       K   P   S   L   S   A   Q   P   G   P   A   V   S   S   G   G>
      _____GLYCOPROTEIN VI_____>
```

Figure 7B

```
                   _____DOMAIN 2_____>
                             12/19
         390       400       410       420       430
    GACGTAACCCTACAGTGTCAGACTCGGTATGGCTTTGACCAATTTGCT
    CTGCATTGGGATGTCACAGTCTGAGCCATACCGAAACTGGTTAAACGA
     D   V   T   L   Q   C   Q   T   R   Y   G   F   D   Q   F   A>
                   _____GLYCOPROTEIN VI_____>
                             ____DOMAIN 2_____>

440       450       460       470       480
    CTGTACAAGGAAGGGGACCCTGCGCCCTACAAGAATCCCGAGAGATGG
    GACATGTTCCTTCCCCTGGGACGCGGGATGTTCTTAGGGCTCTCTACC
     L   Y   K   E   G   D   P   A   P   Y   K   N   P   E   R   W>
                   _____GLYCOPROTEIN VI_____>
                             ____DOMAIN 2_____>

490       500       510       520
    TACCGGGCTAGTTTCCCCATCATCACGGTGACCGCCGCCCACAGCGGA
    ATGGCCCGATCAAAGGGGTAGTAGTGCCACTGGCGGCGGGTGTCGCCT
     Y   R   A   S   F   P   I   I   T   V   T   A   A   H   S   G>
                   _____GLYCOPROTEIN VI_____>
                             ____DOMAIN 2_____>

530       540       550       560       570
    ACCTACCGATGCTACAGCTTCTCCAGCAGGGACCCATACCTGTGGTCG
    TGGATGGCTACGATGTCGAAGAGGTCGTCCCTGGGTATGGACACCAGC
     T   Y   R   C   Y   S   F   S   S   R   D   P   Y   L   W   S>
                   _____GLYCOPROTEIN VI_____>
                             ____DOMAIN 2_____>

580       590       600       610       620
    GCCCCCAGCGACCCCCTGGAGCTTGTGGTCACAGGAACCTCTGTGACC
    CGGGGGTCGCTGGGGGACCTCGAACACCAGTGTCCTTGGAGACACTGG
     A   P   S   D   P   L   E   L   V   V   T   G   T   S   V   T>
                   _____GLYCOPROTEIN VI_____>
                         ____DOMAIN 2_____>

>T655C
                                       |
         630       640       650     |  660       670
    CCCAGCCGGTTACCAACAGAACCACCTTCCTCGGTAGCAGAATTCTCA
    GGGTCGGCCAATGGTTGTCTTGGTGGAAGGAGCCATCGTCTTAAGAGT
       P   S   R   L   P   T   E   P   P   S   S   V   A   E   F   S>
                   _____GLYCOPROTEIN VI_____>

>A709G
                                       |
         680       690       700     |  710       720
    GAAGCCACCGCTGAACTGACCGTCTCATTCACAAACAAAGTCTTCACA
    CTTCGGTGGCGACTTGACTGGCAGAGTAAGTGTTTGTTTCAGAAGTGT
     E   A   T   A   E   L   T   V   S   F   T   N   K   V   F   T>
                   _____GLYCOPROTEIN VI_____>

>A745G
                                |
         730       740       |  750       760
    ACTGAGACTTCTAGGAGTATCACCACCAGTCCAAAGGAGTCAGACTCT
    TGACTCTGAAGATCCTCATAGTGGTGGTCAGGTTTCCTCAGTCTGAGA
     T   E   T   S   R   S   I   T   T   S   P   K   E   S   D   S>
                   _____GLYCOPROTEIN VI_____>
```

Figure 7C

```
       770        780        790        800        810
CCAGCTGGTCCTGCCCGCCAGTACTACACCAAGGGCAACCTGGTCCGG
GGTCGACCAGGACGGGCGGTCATGATGTGGTTCCCGTTGGACCAGGCC
   P  A  G  P  A  R  Q  Y  Y  T  K  G  N  L  V  R>
   _____GLYCOPROTEIN VI_____>
                                              _____>

820        830        840        850        860
ATATGCCTCGGGGCTGTGATCCTAATAATCCTGGCGGGGTTTCTGGCA
TATACGGAGCCCCGACACTAGGATTATTAGGACCGCCCCAAAGACCGT
   I  C  L  G  A  V  I  L  I  I  L  A  G  F  L  A>
   _____GLYCOPROTEIN VI_____>
                  _____TRANSMEMBRANE_____>

870        880        890        900        910
GAGGACTGGCACAGCCGGAGGAAGCGCCTGCGGCACAGGGGCAGGGCT
CTCCTGACCGTGTCGGCCTCCTTCGCGGACGCCGTGTCCCCGTCCCGA
   E  D  W  H  S  R  R  K  R  L  R  H  G  R  A>
   _____GLYCOPROTEIN VI_____>

>A950T
                                          |
       920        930        940        950        960
GTGCAGAGGCCGCTTCCGCCCCTGCCGCCCCTCCCGCAGACCCGGAAA
CACGTCTCCGGCGAAGGCGGGGACGGCGGGGAGGGCGTCTGGGCCTTT
      V  Q  R  P  L  P  P  L  P  P  L  P  Q  T  R  K>
      _____GLYCOPROTEIN VI_____>

>C964A
  |
  |    970        980        990       1000
TCACACGGGGGTCAGGATGGAGGCCGACAGGATGTTCACAGCCGCGGG
AGTGTGCCCCCAGTCCTACCTCCGGCTGTCCTACAAGTGTCGGCGCCC
   S  H  G  G  Q  D  G  G  R  Q  D  V  H  S  R  G>
   _____GLYCOPROTEIN VI_____>

1010       1020       1030       1040       1050
TTATGTTCATGACCGCTGAACCCCAGGCACGGTCGTATCCAAGGGAGG
AATACAAGTACTGGCGACTTGGGGTCCGTGCCAGCATAGGTTCCCTCC
   L  C  S>
   _____>

1060       1070       1080
GATCATGGCATGGGAGGCGACTCATGAGGGCAC
CTAGTACCGTACCCTCCGCTGAGTACTCCCGTG
```

Figure 8A

Allele a, encoding LSKTQH

ATGTCTCCATCCCCGACCGCCCTCTTCTGTCTTGGGCTGTGTCTGGGGCGT
GTGCCAGCGCAGAGTGGACCGCTCCCCAAGCCCTCCCTCCAGGCTCTGCC
CAGCTCCCTGGTGCCCCTGGAGAAGCCAGTGACCCTCCGGTGCCAGGGAC
CTCCGGGCGTGGACCTGTACCGCCTGGAGAAGCTGAGTTCCAGCAGGTAC
CAGGATCAGGCAGTCCTCTTCATCCCGGCCATGAAGAGAAGTCTGGCTGG
ACGCTACCGCTGCTCCTACCAGAACGGAAGCCTCTGGTCCCTGCCCAGCG
ACCAGCTGGAGCTCGTTGCCACGGGAGTTTTTGCCAAACCCTCGCTCTCAG
CCCAGCCCGGCCCGGCGGTGTCGTCAGGAGGGGACGTAACCCTACAGTGT
CAGACTCGGTATGGCTTTGACCAATTTGCTCTGTACAAGGAAGGGGACCC
TGCGCCCTACAAGAATCCCGAGAGATGGTACCGGGCTAGTTTCCCCATCA
TCACGGTGACCGCCGCCCACAGCGGAACCTACCGATGCTACAGCTTCTCC
AGCAGGGACCCATACCTGTGGTCGGCCCCAGCGACCCCCTGGAGCTTGT
GGTCACAGGAACCTCTGTGACCCCAGCCGGTTACCAACAGAACCACCTT
CCTCGGTAGCAGAATTCTCAGAAGCCACCGCTGAACTGACCGTCTCATTC
ACAAACAAAGTCTTCACAACTGAGACTTCTAGGAGTATCACCACCAGTCC
AAAGGAGTCAGACTCTCCAGCTGGTCCTGCCCGCCAGTACTACACCAAGG
GCAACCTGGTCCGGATATGCCTCGGGGCTGTGATCCTAATAATCCTGGCG
GGGTTTCTGGCAGAGGACTGGCACAGCCGGAGGAAGCGCCTGCGGCACA
GGGGCAGGGCTGTGCAGAGGCCGCTTCCGCCCCTGCCGCCCCTCCCGCAG
ACCCGGAAATCACACGGGGGTCAGGATGGAGGCCGACAGGATGTTCACA
GCCGCGGGTTATGTTCATGACCGCTGAACCCCAGGCACGGTCGTATCCAA
GGGAGGGATCATGGCATGGGAGGCGACTCATGAGGGCAC

Allele a', encoding VSKTQH

ATGTCTCCATCCCCGACCGCCCTCTTCTGTCTTGGGCTGTGTCTGGGGCGT
GTGCCAGCGCAGAGTGGACCGCTCCCCAAGCCCTCCCTCCAGGCTCTGCC
CAGCTCCCTGGTGCCCCTGGAGAAGCCAGTGACCCTCCGGTGCCAGGGAC
CTCCGGGCGTGGACCTGTACCGCCTGGAGAAGCTGAGTTCCAGCAGGTAC
CAGGATCAGGCAGTCCTCTTCATCCCGGCCATGAAGAGAAGTCTGGCTGG
ACGCTACCGCTGCTCCTACCAGAACGGAAGCCTCTGGTCCCTGCCCAGCG
ACCAGGTGGAGCTCGTTGCCACGGGAGTTTTTGCCAAACCCTCGCTCTCAG
CCCAGCCCGGCCCGGCGGTGTCGTCAGGAGGGGACGTAACCCTACAGTGT
CAGACTCGGTATGGCTTTGACCAATTTGCTCTGTACAAGGAAGGGGACCC
TGCGCCCTACAAGAATCCCGAGAGATGGTACCGGGCTAGTTTCCCCATCA
TCACGGTGACCGCCGCCCACAGCGGAACCTACCGATGCTACAGCTTCTCC
AGCAGGGACCCATACCTGTGGTCGGCCCCAGCGACCCCCTGGAGCTTGT
GGTCACAGGAACCTCTGTGACCCCAGCCGGTTACCAACAGAACCACCTT
CCTCGGTAGCAGAATTCTCAGAAGCCACCGCTGAACTGACCGTCTCATTC
ACAAACAAAGTCTTCACAACTGAGACTTCTAGGAGTATCACCACCAGTCC
AAAGGAGTCAGACTCTCCAGCTGGTCCTGCCCGCCAGTACTACACCAAGG
GCAACCTGGTCCGGATATGCCTCGGGGCTGTGATCCTAATAATCCTGGCG
GGGTTTCTGGCAGAGGACTGGCACAGCCGGAGGAAGCGCCTGCGGCACA
GGGGCAGGGCTGTGCAGAGGCCGCTTCCGCCCCTGCCGCCCCTCCCGCAG

Figure 8B

```
ACCCGGAAATCACACGGGGGTCAGGATGGAGGCCGACAGGATGTTCACA
GCCGCGGGTTATGTTCATGACCGCTGAACCCCAGGCACGGTCGTATCCAA
GGGAGGGATCATGGCATGGGAGGCGACTCATGAGGGCAC
```

Allele b, encoding LPEALN

```
ATGTCTCCATCCCCGACCGCCCTCTTCTGTCTTGGGCTGTGTCTGGGGCGT
GTGCCAGCGCAGAGTGGACCGCTCCCCAAGCCCTCCCTCCAGGCTCTGCC
CAGCTCCCTGGTGCCCCTGGAGAAGCCAGTGACCCTCCGGTGCCAGGGAC
CTCCGGGCGTGGACCTGTACCGCCTGGAGAAGCTGAGTTCCAGCAGGTAC
CAGGATCAGGCAGTCCTCTTCATCCCGGCCATGAAGAGAAGTCTGGCTGG
ACGCTACCGCTGCTCCTACCAGAACGGAAGCCTCTGGTCCTGCCCAGCG
ACCAGCTGGAGCTCGTTGCCACGGGAGTTTTTGCCAAACCCTCGCTCTCAG
CCCAGCCCGGCCCGGCGGTGTCGTCAGGAGGGGACGTAACCCTACAGTGT
CAGACTCGGTATGGCTTTGACCAATTTGCTCTGTACAAGGAAGGGGACCC
TGCGCCCTACAAGAATCCCGAGAGATGGTACCGGGCTAGTTTCCCCATCA
TCACGGTGACCGCCGCCCACAGCGGAACCTACCGATGCTACAGCTTCTCC
AGCAGGGACCCATACCTGTGGTCGGCCCCAGCGACCCCCTGGAGCTTGT
GGTCACAGGAACCTCTGTGACCCCAGCCGGTTACCAACAGAACCACCTT
CCTTGGTAGCAGAATTCTCAGAAGCCACCGCTGAACTGACCGTCTCATTCA
CAAACGAAGTCTTCACAACTGAGACTTCTAGGAGTATCACCGCCAGTCCA
AAGGAGTCAGACTCTCCAGCTGGTCCTGCCCGCCAGTACTACACCAAGGG
CAACCTGGTCCGGATATGCCTCGGGGCTGTGATCCTAATAATCCTGGCGG
GGTTTCTGGCAGAGGACTGGCACAGCCGGAGGAAGCGCCTGCGGCACAG
GGGCAGGGCTGTGCAGAGGCCGCTTCCGCCCCTGCCGCCCCTCCCGCTGA
CCCGGAAATCAAACGGGGGTCAGGATGGAGGCCGACAGGATGTTCACAG
CCGCGGGTTATGTTCATGACCGCTGAACCCCAGGCACGGTCGTATCCAAG
GGAGGGATCATGGCATGGGAGGCGACTCATGAGGGCAC
```

DIAGNOSIS OF ABNORMAL BLOOD CONDITIONS BASED ON POLYMORPHISMS IN THE GLYCOPROTEIN VI GENE

This invention relates to the diagnosis of abnormal blood conditions, in particular to diagnosis of an increased risk of bleeding.

Glycoprotein VI (GPVI) plays a crucial role in platelet activation and aggregation. Deficiency of GPVI is associated with a mild bleeding phenotype and a major reduction in the response to collagen on platelets (Moroi et al, 1989). GPVI is a 63 kDa type I transmembrane platelet glycoprotein and is the major signalling receptor for collagen on platelets (Watson et al, 2001). The mature GPVI protein consists of 319 amino acids, the first 185 encoding two immunoglobulin (Ig)-like C2 type folds, a highly glycosylated stem of 64 amino acids, an arginine containing 19 amino acid transmembrane domain and a 51 amino acid cytoplasmic domain (Clemetson et al, 1999). Collagen binds GPVI via the two tandem Ig-like domains and clustering of GPVI upon interaction with collagen results in signalling via the γ chain of the FcεR.

The GPVI gene has multiple alleles, but two of these are frequently used in Caucasians: GPVI$^a$ and GPVI$^b$. The cDNA sequences of these alleles are shown in FIG. 8, and the cDNA sequence and translation of the GPVI$_a$ allele is shown in FIG. 7. The proteins encoded by the GPVI$_a$ and GPVI$_b$ alleles differ by five amino acids. Three of these are in the stem (S219P, K237E, T249A), and two are in the cytoplasmic domain (Q317L and H322N). Croft et al, 2001, have reported that homozygosity for the 'b' allele encoding P219 (referred to as T13254C by Croft et al, 2001) is associated with an increased risk of myocardial infarction, particularly in older female individuals.

Collagen related peptide (CRP, a triple-helical peptide containing a glycine-proline-hydroxyproline repeat motif) acts specifically via GPVI to activate platelets, and results in a signalling cascade very similar to that evoked by native collagen Kehrel et al, 1998; Knight et al, 1999). We observed a significant inter-individual variation in the platelet aggregation response to CRP, and measurement of the GPVI expression in 89 Caucasoids with a recombinant human antibody showed a three-fold variation. We postulated that these differences may be associated with the presence of different GPVI alleles. To address this question we performed a high resolution single nucleotide polymorphism (SNP) map of the GPVI gene from 188 chromosomes. This confirmed the presence of two frequently used alleles with frequencies of 0.85 (allele 'a', wild-type allele) and 0.13 (allele b, low frequency allele) (recent studies have found the frequencies to be 0.79 and 0.18, respectively), together with a number of rare alleles which most likely arose by conversion and crossing-over. Genotyping of 1153 Caucasians for all 5 amino acid replacement mutations resulted in the identification of 28 normal donors homozygous for the low frequency allele.

We compared GPVI expression between donors homozygous for these two alleles and observed that the most common allele, encoding SKTQH (SEQ ID NO: 85) (n=7 matched donors homozygous for the minor allele PEALN (SEQ ID NO: 86)), showed a significantly higher GPVI expression. The difference in GPVI expression was associated with an approximately ten-fold difference in the dose-response to CRP. This difference although less prominent was confirmed when collagen type I (ethicon) was used to induce aggregation and in thrombin generation assays . Not surprisingly the difference was reflected in several events downstream of GPVI activation, including α granule release as measured by expression of P selectin, and binding of fibrinogen and annexin V.

The observation that the GPVI$^{bb}$ genotype is associated with less responsive platelets is surprising in the light of the work by Croft et al (2001) reporting a link between this allele and myocardial infarction.

According to the invention there is provided a method of diagnosing whether a subject has, or is at risk of, an abnormal blood condition associated with an increased risk of bleeding which comprises determining the GPVI allelotype of the subject to determine whether the subject is homozygous or heterozygous for the GPVI$^b$ allele.

Platelets of subjects who are homozygous for the GPVI$^b$ allele have a reduced ability to respond to CRP and to induce thrombin generation. Such individuals are thought to have an increased risk of bleeding. It is also possible that subjects who are heterozygous for the GPVI$^b$ allele have an increased risk of bleeding.

The GPVI allelotype of the subject may be determined by any suitable method. In a preferred method, one or more single nucleotide polymorphisms (SNPs) which are distinctive of a GPVI allele are detected for (suitably by genotyping of nucleic acid, preferably DNA, encoding GPVI) in order to determine the GPVI allelotype. Preferably the or each SNP which is detected for is selected from the five SNPs which give rise to amino acid differences between the protein expression products of the GPVI$^a$ and GPVI$^b$ alleles (there are other SNPs of the GPVI gene which are not associated with amino acid changes). The five SNPs are at positions 655, 709, 745, 950, and 964 of the GPVI cDNA sequence (these correspond to positions 13010, 9570, 22524, 23246, and 23260 of the GPVI genomic sequence, respectively, and positions 199, 217, 229, 297, and 302 of the amino acid sequence, respectively (see Table 4), or positions 219, 237, 249, 317, and 322 of the amino acid sequence, respectively, if the signal peptide is included (see FIG. 7)). FIG. 7 shows the wild-type GPVI (GPVI$^a$) cDNA sequence and translation—the SNPs that encode amino acid substitutions are marked. The cDNA sequences of the GPVI$^a$ and GPVI$^b$ alleles are shown in FIG. 8. The GPVI$^a$ allele contains T at 655, A at 709, A at 745, A at 950, and C at 964. The GPVI$^b$ allele contains C at 655, G at 709, G at 745, T at 950, and A at 964. The amino acids encoded by the SNPs at positions 655, 709, 745, 950, and 964 of the GPVI cDNA sequence are at positions 219, 237, 249, 317, and 322 of the GPVI amino acid sequence (see FIG. 7). The GPVI$^a$ allele protein expression product contains S at 219, K at 237, T at 249, Q at 317, and H at 322. The GPVI$^b$ allele protein expression product contains P at 219, E at 237, A at 249, L at 317, and N at 322.

From the study reported in the Example 1 below, the distribution of GPVI allelotypes in Caucasians was calculated to be 65% (755/1153) GPVI$^{aa}$, 25% (288/1153) GPVI$^{ab}$, 2% (23/1153) GPVI$^{bb}$, and 7% (80/1153) rare alleles (shown schematically in FIG. 11). The rare alleles are thought to have arisen from conversion or crossing over. The existence of rare alleles means that a test in which a single SNP distinctive of the GPVI$^a$ or GPVI$^b$ alleles is detected for to determine whether the subject has a GPVI$^{aa}$, GPVI$^{ab}$, or GPVI$^{bb}$ allelotype would give a false result for a subject with a rare allelotype. Because the frequency of rare alleles was found to be 7% in the Caucasoid population examined, the accuracy of such a test may be considered to be unacceptably low for clinical use. In order to increase the accuracy of the test, it is necessary to test for more than one SNP. Most preferably, all five SNPs which give rise to amino acid differences between the protein expression products of the GPVI$^a$ and GPVI$^b$ alleles are detected for.

In the study reported in Example 2 below, an additional 183 individuals (1127 Caucasians, 63 Koreans, 40 South African blacks, 40 Ethiopians and 40 Curacao) were investigated to fully characterise variation in GPVI. Based on the typing of the core panel of 1,127 Caucasoid it was concluded that for a reliable assignment of a GPVI core haplotype of 5 non-synonymous SNPs, testing on at least two SNPs is required. An over 99.5% reliability of haplotype assignment can be achieved when testing is performed at position T13010C (S199P) and at position A23246T (Q297L). Thus, where the subject is a Caucasian, preferably at least two SNPs which are distinctive of the GPVI$^b$ allele are detected for. Preferably the SNPs are at positions 13010 and 23246 of the genomic sequence.

There is a high level of haplotype diversity in several non-Caucasoid populations. SNP typing at preferably all 5 replacement mutations is required for a reliable assignment of the haplotype in many of these other populations, i.e. South African blacks, Ethiopian blacks, Dutch Antilles and several Far Eastern populations. Thus, where the subject is non-Caucasian, preferably all 5 SNPs which are distinctive of the GPVI$^b$ allele and give rise to amino acid differences between the protein expression products of the GPVI$^a$ and GPVI$^b$ alleles are detected for.

We have also observed that there is in Caucasians a poor correlation between the SNP at position C-154T (Promoter mutation) and the core haplotype as defined by T13010C (S199P) and A23246T (Q297L). The former (C-154T) should not, therefore, be used to reliably predict expression levels of GPVI.

Detection for the, or each SNP may be carried out using any suitable method. Suitable in vitro methods of SNP detection known to those of ordinary skill in the art include real-time PCR, fluorimetric analysis, restriction enzyme analysis, restriction fragment length polymorphism (RFLP), single strand conformation polymorphism (SSCP), or use of a probe (preferably a labelled probe) which hybridises specifically to a region of nucleic acid which includes an SNP, use of a micro array comprising a probe which hybridises specifically to a region of nucleic acid which includes an SNP, and sequencing of nucleic acid SNPs may be detected for in genomic DNA, RNA (for example platelet mRNA or total RNA), cDNA, or nucleic acid amplified from genomic DNA, RNA, or cDNA. Nucleic acid amplification may be carried out using any suitable method, for example the PCR, ligase chain reaction, or 3SR methods.

In other methods for determining GPVI allelotype, the presence of a protein product encoded by a GPVI allele may be detected for. This may be achieved by use of an antibody, or fragment or derivative thereof, specific for the protein expression product. An antibody, or fragment or derivative, is specific for a protein expression product of a GPVI allele if it can be used to distinguish one GPVI allele expression product from another. Preferably the antibody, or fragment or derivative thereof, is able to distinguish the GPVI$^a$ and GPVI$^b$ allele protein expression products.

Specific antibodies may be obtained by use of a polypeptide with an amino acid sequence corresponding to the sequence of a region of a GPVI allele protein expression product which includes an amino acid residue encoded by an SNP distinctive of the GPVI allele. Preferably the polypeptide includes an amino acid sequence corresponding to a region which includes any of the following positions of the GPVI$^a$ or GPVI$^b$ allele protein expression product: 219, 237, 249, 317 and 322. Preferably the polypeptide is 4-100, more preferably 7-50 amino acids in length.

In other methods, the presence of the protein expression product of a GPVI allele may be detected for on the basis of its molecular weight, for example by using comparative electrophoretic mobility or mass spectrometry, or using isoelectric focusing. It is possible that the molecular weight of the two allele protein expression products may vary due to differences in glycosylation, in particular the GPVI$^a$ allele product may be heavier than the GPVI$^b$ allele product as a result of two potential extra O-glycosylation sites present in the GPVI$^a$ allele product. The allele protein expression products also differ in charge, because of the polymorphism at position 217.

In further methods, the GPVI allelotype of the subject may be determined by measuring the total expression of GPVI in platelets of the subject. The level of expression of the GPVI$^b$ allele is much lower than the GPVI$^a$ allele. Expression could be measured, for example by Western blotting using the antibodies 10B12 and 1C3 (described in Example 3 below) as described in Joutsi-Korhonen et al (Blood, Jan. 30, 2003). An advantage of such methods is that specific antibodies able to distinguish the GPVI$^a$ and GPVI$^b$ allele protein expression products are not required.

According to the invention there is also provided an antibody specific for a protein expression product of a GPVI$^a$ allele, or fragment or derivative thereof. There is also provided an antibody specific for a protein expression product of a GPVI$^b$ allele, or fragment or derivative thereof. Such antibodies can be used in a method of the invention for diagnosing whether a subject has, or is at risk of, an abnormal blood condition associated with an increased risk of bleeding.

There is also provided according to the invention an abnormal blood condition diagnosis kit which comprises means for determining the GPVI allelotype of a subject to determine whether the subject is homozygous or heterozygous for the GPVI$^b$ allele, wherein the abnormal blood condition is associated with an increased risk of bleeding.

The invention also provides a kit for diagnosing whether a subject has, or is at risk of, an abnormal blood condition associated with an increased risk of bleeding, which comprises means for determining the GPVI allelotype of the subject to determine whether the subject is homozygous or heterozygous for the GPVI$^b$ allele, wherein the determining means allow detection of two or more SNPs, or amino acids encoded by two or more SNPs, which are distinctive of the GPVI$^b$ allele. The kit may further comprise determining means for detection of two or more SNPs, or amino acids encoded by two or more SNPs of the GPVI$^a$ allele. Preferably the determining means allow detection of SNPs at positions 655, 709, 745, 950, and 964 of the cDNA sequence (or positions 13010, 19570, 22524, 23246, and 23260 of the genomic sequence).

The invention also provides a corresponding method for diagnosing whether a subject has, or is at risk of, an abnormal blood condition associated with an increased risk of bleeding, which comprises determining the GPVI allelotype of the subject to determine whether the subject is homozygous or heterozygous for the GPVI$^b$ allele, wherein two or more SNPs, or amino acids encoded by two or more SNPs, which are distinctive of the GPVI$^b$ allele are detected for.

Where a kit or method of the invention is for diagnosing a Caucasian, preferably the determining means is for detection of SNPs at genomic nucleotides 13010 and 23246. Where a kit or method of the invention is for diagnosing a non-Caucasian, preferably the determining means is for detection of SNPs at genomic nucleotides 13010, 19570, 22524, 23246, and 23260.

The determining means may include a probe capable of hybridising specifically to a region of GPVI nucleic acid which includes an SNP distinctive of a GPVI allele. The probe preferably comprises nucleic acid consisting of 8-50 nucleotides. The probe preferably hybridises under stringent conditions. Stringent conditions are defined herein as 0.1× SSC, 0.1% SDS at 65 degrees C. The determining means may include an antibody, or fragment or derivative thereof, which is specific to the protein expression product of a GPVI allele. The determining means may include probes and primers required for detection of the SNPs by real-time PCR.

The kits may be provided with all the reagents necessary for the determination of the GPVI allelotype. For example, the kits may include oligonucleotide primers for amplification of nucleic acid which includes an SNP to be detected for, labels for detection of bound antibodies, or probes, reagents for isolating or obtaining genomic DNA, mRNA or cDNA from a biological sample obtained from the subject.

The kits may be provided with instructions for the use thereof as a test to diagnose whether a subject has, or is at risk of, an abnormal blood condition associated with an increased risk of bleeding.

There is further provided according to the invention use of a probe capable of binding specifically to a region of GPVI nucleic acid which includes an SNP distinctive of a GPVI allele for the diagnosis of an abnormal blood condition.

Subjects who are homozygous for the GPVI$^b$ allele are termed herein easy bruisers (EBs). Such individuals may be normal healthy individuals, but the EB phenotype may be of major clinical significance if normal haemostasis is challenged. EB identification is also expected to be of clinical use in certain categories of patients.

Identification of GPVI allelotype is expected to be of value for the following categories of individuals:

i) Patients with a low platelet count (i.e. <50×10$^9$/L) because of reduced generation of platelets by the bone marrow (i.e. cancer patients because of bone marrow infiltration or iatrogenic), increased destruction of platelets (i.e. patients with antibody-mediated thrombocytopenia's), or increased consumption (i.e. patients with disseminated intravascular coagulation) or hyperslenism;

ii) Patients undergoing major surgical procedures known for a high risk of significant blood loss (i.e. cardio-thoracic surgery; orthopedic surgery, certainly the category of redo's; organ transplantation, especially liver, heart and lung, but possibly kidney; surgery of trauma patients; brain surgery inclusive invasive imaging; vessel surgery);

iii) Patients with an inherited bleeding disorder such as haemophilia A or B, Von Willebrands' disease and other rarer forms (i.e. Glanzmann thrombasthenia) or with acquired coagulopathies (i.e. liver disease, viral hepatitis);

iv) Patients receiving blood thinning drugs (anti-coagulants, anti-platelet drugs, thrombolytic drugs) to reduce the risk of venous and/or arterial thrombosis. One of the major unwanted side effects of these drugs is bleeding. Cerebral bleeds or bleeds in other vital organs can cause life-long disability or even death;

v) Donors who give blood by routine donation or blood derivatives by apheresis technology. One of the most frequent complaints of donors is serious bruising post-donation at the site of venepuncture.

If a patient is an EB, special precautions can be taken. Some examples are:

i) In surgery: increase availability of donor blood, consider additional drugs (i.e. DDAVP, Tranexamic Acid) to reduce the risk of excess bleeding;

ii) In patients with low platelets because of low endogenous production. Increase platelet transfusion trigger. Currently, donor platelets are generally given when the platelet count is <10×10$^9$/L (higher if patient is unstable). However, in an EB a more conservative level of 20×10$^9$/L could be used. This may reduce the chance of serious bleeding without causing an unacceptable increase in platelet demand. Similarly, platelet levels required to cover invasive procedures could be tailored better to the patient depending on the GPVI genotype;

iii) In patients with low platelets because of antibody-mediated destruction of platelet. Treatment for autoantibody mediated thrombocytopenia is based on a combination of the platelet count and clinical signs of bleeding. However, in patients with very low platelet counts (20×10$^9$/L) treatment is given to reduce the risk of serious bleeding, even in the absence of bleeding. In these patients expensive therapies or therapies with major side effects are prescribed to reduce the relatively small risk of bleeding. Stratifying of these therapies on basis of the GPVI genotype may be possible;

iv) The prophylactic treatment regime in Haemophilia patients may be better tailored to the patient. In addition life-style advice could be modified depending on the GPVI genotype;

v) Patients on blood thinning drugs (these include anti-coagulants, anti-platelet drugs or thrombolytic drugs, or inhibitors of collagen-mediated platelet activation, such as a drugs directed to: GPVI (such as antibodies 10B12 and 1C3, described below); proteins associated directly with the intracellular domains of GpVI (for example src family kinases such as fyn); proteins that associate with FcR gamma (tyrosine kinase: p72syk; adaptors: LAT or SLP-76); or proteins downstream from them in GPVI-mediated signalling (PI3-kinase, phospholipase C gamma 2) (Watson S. P. Collagen receptor signaling in platelets and megakaryocytes, Thrombosis and Haemostasis 1999, vol 82 pp 365-376)). Patients with an EB genotype may require reduced dosing with these drugs. There are no effective antidotes for several of these drugs (i.e. Clopridogel, GPI-IbIIIa antagonists, Tissue plasminogen activator, Streptokinase). Overdosing is an issue of serious concern and the therapeutic range of several of the drugs is relatively narrow. Dosing schedules may be adjusted on the basis of the GPVI genotype. Moreover, many novel 'blood thinning' drugs are being trialed or are under development. Whether these novel drugs will enter the market will depend on their clinical effectiveness and more importantly on the incidence and severity of side effects (bleeding being the most important). Pharmaceutical industries will therefore have an interest to identify those patients at risk of bleeding. The GPVI genetic marker may be one of these.

vi) In donors. Blood services may more carefully manage donors with an EB genotype. In addition platelets from donors with an EB genotype may be less effective in preventing bleeding in the recipient when compared with platelets from 'normal' donors. GPVI bb donors may be barred from giving platelets.

According to the invention there is also provided a method of determining the GPVI allelotype of a subject which comprises detecting for at least one single nucleotide polymorphism (SNP) which is distinctive of a GPVI allele. The SNP or SNPs may be selected from, any, or any combination of the SNPs identified in Table 4. In a preferred method, nucleic acid (preferably DNA) encoding GPVI is genotyped for the, or each SNP.

Embodiments of the invention are now described, by way of example only, with reference to the accompanying drawings in which:

FIG. 1 shows GPVI expression on platelets in 89 random donors. Anti-GPVI specific scFv 1C3 was used in flow cytometry. The GPVI level is presented as median fluorescence intensity, the mean being 13.09 (SD 3.49, CI95% 12.4-13.8). Samples (all but one) were genotyped for GPVI: 58 were homozygous for the 'a' allele (SKTQH) (SEQ ID NO: 85), one was homozygous for the 'b' allele (PEALN) (SEQ 1D NO: 86) and 22 were heterozygous. The GPVI expression levels of the 'aa' donors (mean 13.5, SD 3.5, CI95% 12.6-14.5) were non-significantly higher than the 'ab' donors (mean 11.9, SD 3.1, CI95% 10.5-13.2; Mann-Whitney U test p=0.084).

FIG. 2 shows the platelet GPVI and GPIaIIa expression levels in 'aa' and 'bb' donors. GPVI specific scFv 1C3 (A.) and scFv 10B12 (B.) and GPIaIIa specific antibody NBS-P16 (C.) were used in flow cytometry. The levels are presented as median fluorescence intensity related to the negative antibody control, 9E10, of each sample. The GPVI levels differed significantly between the 'aa' (n=8) and the 'bb' (n=7) donors, studied both with scFv 1C3 (Mann-Whitney U test, p=0.014) and 10B12 (p=0.006). With scFv 1C3, for the 'aa' and the 'bb' donors the mean relative fluorescence intensities were 8.9 (SD 1.7, CI95% 7.5-10.3) and 6.1 (SD 1.4, CI95% 4.8-7.4), respectively. With scFv 10B12, for the 'aa' and the 'bb' donors the mean relative fluorescence intensities were 7.6 (SD 1.2, CI95% 6.6-8.6) and 5.4 (SD 0.9, CI95% 4.5-6.2), respectively. There was no difference between the 'aa' and 'bb' donors in GPIaIIa expression.

FIG. 3 shows a comparison of GPVI and GPIaIIa platelet expression levels on genotyped samples. The binding of GPIaIIa levels (n=15, mean FL1 32.2, SD 10.4, CI95% 27.5-39.0) varied more than the GPVI levels (n=15, mean FL1 7.5, SD 2.0, CI95% 6.4-8.5). There was no obvious correlation between GPIaIIa and GPVI levels (Spearman correlation, R=0.37).

FIG. 4 shows platelet aggregation with GPVI genotyped 'aa' and 'bb' donors. The platelet aggregation was induced by CRP(A.), collagen type I, Ethicon (B.) or ADP (C.). All 7 'b' homozygotes require a near [1]log more CRP to induce maximum aggregation compared to the 'aa' homozygotes (n=12). The difference was also observed with platelet aggregation responses stimulated with collagen type I (B.). As expected there was no significant difference in the response to ADP (C.).

FIG. 5 shows platelet activation in whole blood induced by CRP studied with flow cytometry. CRP was added to whole blood at 4 different concentrations and the activation markers were tested on CD61 positive events. For all three markers there was a clear dose-response relation (A, B, C). The platelets from 'aa' individuals (n=7) bound more fibrinogen (A) and more annexin V (C) after stimulation with CRP (at 0.05 µg/ml and 0.5 µg/ml, respectively) than those from 'bb' donors (Mann-Whitney U test, for fibrinogen, p=0.0061; for annexin V, p=0.0010). Platelet degranulation as measured by the binding of the CD62P moAb after CRP stimulation at 0.05 µg/ml was also significantly different between the two groups (Mann-Whitney U test, p=0.0028; B).

FIG. 6 shows platelet activation in whole blood induced by CRP studied with flow cytometry using annexin V as activation marker. The annexin V positive platelet population comprised a distinct population of cells, increasing dose-dependently: 0 (white), 0, 0.05, 1.0 and 10 µg/ml of CRP. The first, white histogram is without CRP or annexin V.

FIG. 7 shows the wild-type GPVI (the GPVI$^a$ allele) cDNA sequence (SEQ ID NO: 1), complementary sequence (SEQ ID NO: 90) and translation (SEQ ID NO: 2). The SNPs that encode amino acid substitutions are marked;

FIG. 8 shows the cDNA sequence of the GPVI$^a$ allele with L103 (SEQ ID NO: 1), the GPVI$^{a'}$ allele (SEQ ID NO: 4), and the GPVI$^b$ allele (SEQ ID NO: 3).

FIG. 9 shows the GPVI types for 94 sequenced donors;

FIG. 10 shows eight different GPVI variant genotypes;

FIG. 11 shows the distribution of the GPVI genotypes in 1153 Caucasian donors; and FIG. 12 shows the distribution of SNPs throughout the GPVI sequence.

Further evidence in support of the invention is provided in Joutsi-Korhonen et al, Blood 2003: "The low frequency allele of the platelet collagen signalling receptor glycoprotein VI is associated with reduced functional responses and expression".

EXAMPLE 1

Collagen is a major extracellular matrix protein exposed after arterial vessel wall injury. Interaction of platelets with collagen is a multi-step process with tethering over glycoprotein (GP)Ib/DUV via von Willebrand factor, adhesion by interaction with the α2β1 integrin and signalling via GPVI. We have chosen to use collagen related peptide (CRP, triple helical peptide containing glycine-proline-hydroxyproline repeat motifs, generated in our laboratory), which acts specifically via GPVI to activate platelets, and results in a signalling cascade very similar to that evoked by native collagen. Here, we observed significant inter-individual variability in the response to CRP. The GPVI gene has two frequent alleles and genotyping of 1153 Caucasoid showed allele frequencies of 0.85 and 0.13. The two isoforms of GPVI differ by three replacements in the extracellular region proposed to form a glycosylation stem and two in the cytoplasmic domain, by a total of five amino acid replacements. Clustering of GPVI has been postulated to be important for ligand binding and signalling, and various mechanisms may account for the observed signalling differences. For instance, the reduced O-glycosylation which may result from the substitution of S219 or T249, as well as alterations in the main chain of the protein by replacement of S219 with proline. In addition, the Q317L cytoplasmic mutation is thought to be located adjacent to a proposed docking site of the SH3 kinases. Therefore, we investigated allele specific differences in GPVI expression, CRP and collagen mediated aggregation and thrombus formation in whole blood perfusion. We observed a near 10-fold difference in the response to CRP when comparing platelets from 8 high frequency allele homozygotes with 8 low frequency ones. This difference was correlated to, but not dependent on, a difference in GPVI expression as measured with two monoclonal GPVI antibodies and was reflected in all downstream signalling events as measured by the expression of P selectin and the binding of fibrinogen and annexin V.

Results

SNPs in GPVI, GPIa and GPIbα Genes

Of 1153 healthy individuals tested, 65.4% (n=755) were homozygous for the high frequency allele ('aa') and 28 (2.4%) homozygous for the low frequency allele ('bb'). Nineteen individuals were selected for functional studies, 12 of the 'aa' and 7 of the 'bb'. They were also tested for other SNPs: GPVI T-154C, GPIa C-52T GPIa and GPIbα T-5C (Table I).

Interindividual Variation in GPVI Expression

Figure 1:
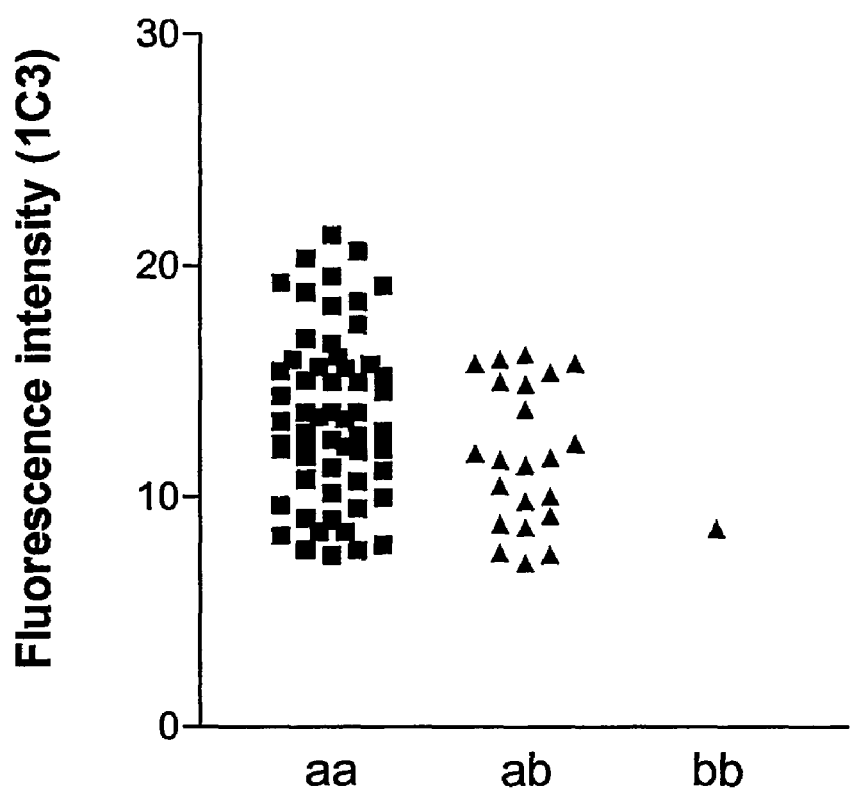

The binding of the GPVI specific scFv 1C3 to isolated platelets from 89 random healthy individuals was assessed by flow cytometry. This showed an approximately three-fold variation in binding (mean FL1 13.1, SD 3.5, CI 95% 12.4-13.8, range 7.11-21.4), suggesting a fairly tight regulation of GPVI expression between different individuals (FIG. 1). All but 8 of the samples (88 of 89 could be tested) were positive for the 'a' allele and the GPVI expression on the single 'b' homozygote was 8.6. The GPVI expression levels of the 'aa' donors (n=58, mean 13.5, SD 3.5, CI95% 12.6-14.5) were non-significantly higher than the 'ab' donors (n=22, mean 11.9, SD 3.1, CI95% 10.5-13.2; Mann-Whitney U test p=0.084).

Expression of GPVI on 'bb' Platelets is Lower than on 'aa' Ones

Figure 2A:
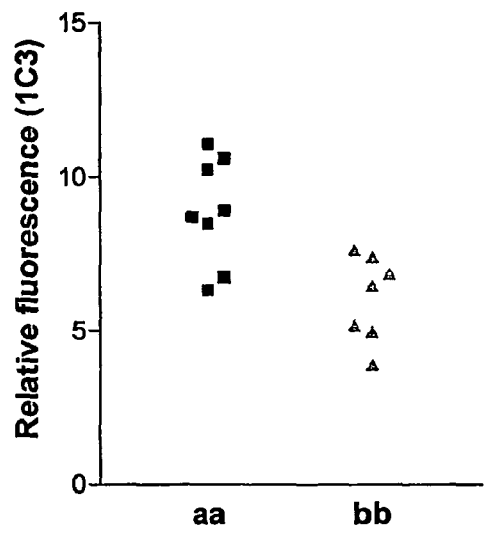
Figure 2B:
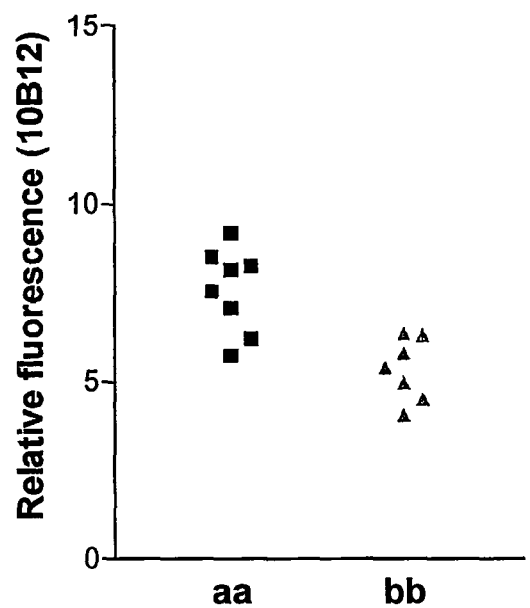
Figure 2C:
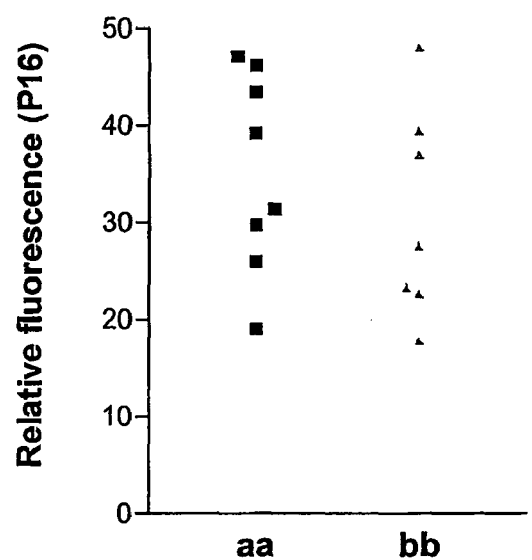

Because of the observed inter-individual differences in scFv 1C3 binding and the low binding to the single 'bb' sample we extended these studies, but included more 'bb' donors. Seven paired 'a' and 'b' homozygous samples were stained with GPVI specific scFvs 1C3 and 10B12 (which recognise non-overlapping GPVI epitopes) and with moAb NBS-P16 (anti-GPIaIIa; FIG. 2). An additional 'aa' sample was included in each run to determine intra-assay variation.

Binding of both scFvs was significantly different between the two groups (Mann-Whitney U test, for 1C3 p=0.014, for 10B12, p=0.006; FIG. 2). With scfv 1C3, for the 'aa' and the 'bb' donors the mean relative fluorescence intensities were 8.9 (SD 1.7, CI95% 7.5-10.3) and 6.1 (SD 1.4, CI95% 4.8-7.4), respectively. With scFy 10B12, for the 'aa' and the 'bb' donors the mean relative fluorescence intensities were 7.6 (SD 1.2, CI95% 6.6-8.6) and 5.4 (SD 0.9, CI95% 4.5-6.2), respectively. The difference remained significant independent whether non-corrected fluorescence intensities were used or ones corrected for the negative control (moAb 9E10), or ones corrected for intra-assay variation.

Figure 3:
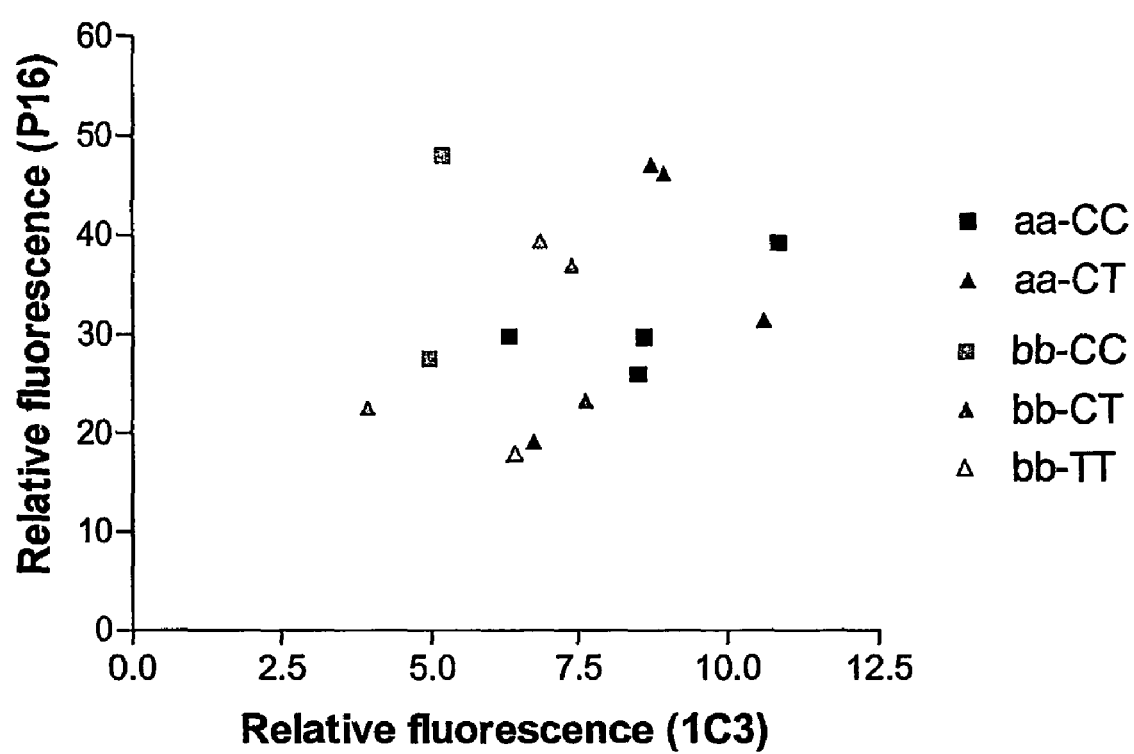

The binding of moAb GPIaIIa levels (n=15, mean FL1 32.2, SD 10.4, CI95% 27.5-39.0) varied more than the GPVI levels (n=15, mean FL1 7.5, SD 2.0, CI95% 6.4-8.5). There was no obvious correlation between GPIaIIa and GPVI levels (Spearman correlation, R=0.37) or between GPIaIa levels and the C-52T SNP of the GPIa gene (FIG. 3).

CRP-Induced Platelet Aggregation

Figure 4:
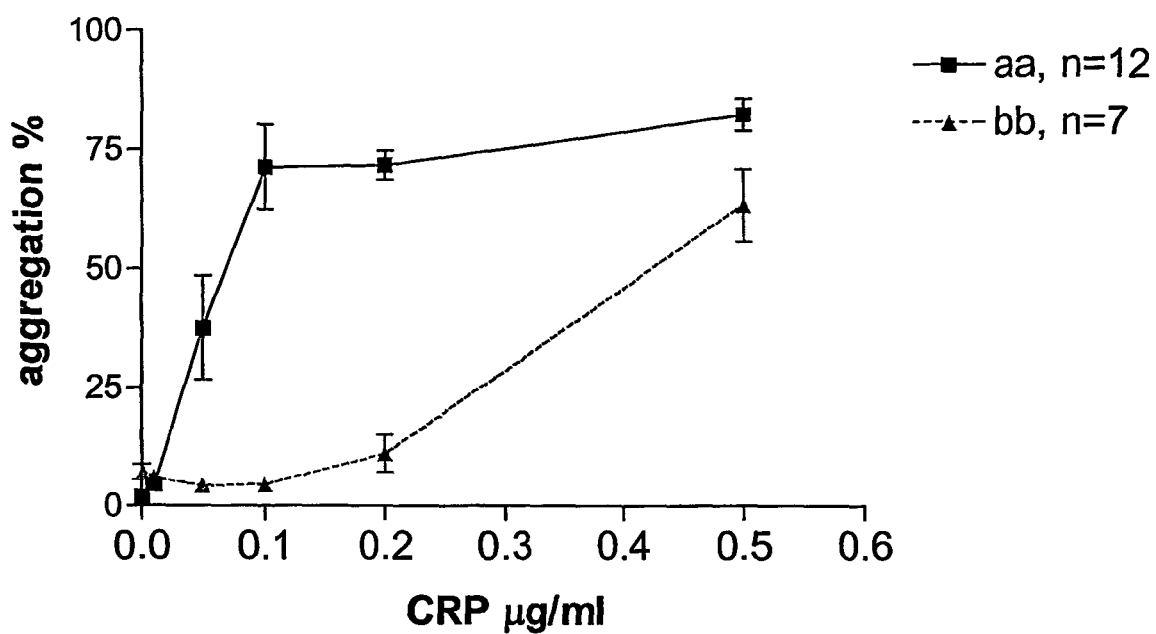

The synthetic collagen-derived triple-helical peptide CRP causes platelet activation by selectively activating GPVL In contrast, ADP activates platelets via G-coupled proteins (Gachet et al, 2001). Inter-individual variation in the response to both agonists has been previously observed in our laboratory, but without an obvious genetic linkage. We determined the dose-response for CRP in platelet aggregation with 19 donors ('aa', n=12; 'bb', n=7). Without exception all 7 'b' homozygotes require a near $^1$log more CRP to induce maximum aggregation compared to the 'aa' homozygotes. Moreover, the differences between the two groups remained statistically significant at three CRP concentrations tested, i.e. 0.05, 0.10 and 0.20 μg/ml (FIG. 4A). For instance, at a CRP concentration of 0.10 μg/ml the mean aggregation for 'aa' platelets was 71% (n=12, SD 31%, range 10-110%, 95% CI 51.6-91.0%) whereas for 'bb' ones 4.6% (n=7, SD 4%, range 1.3-7.8%, 95% CI 1.0-11.0%; Mann Whitney U test p=0.0006).

Figure 4B:
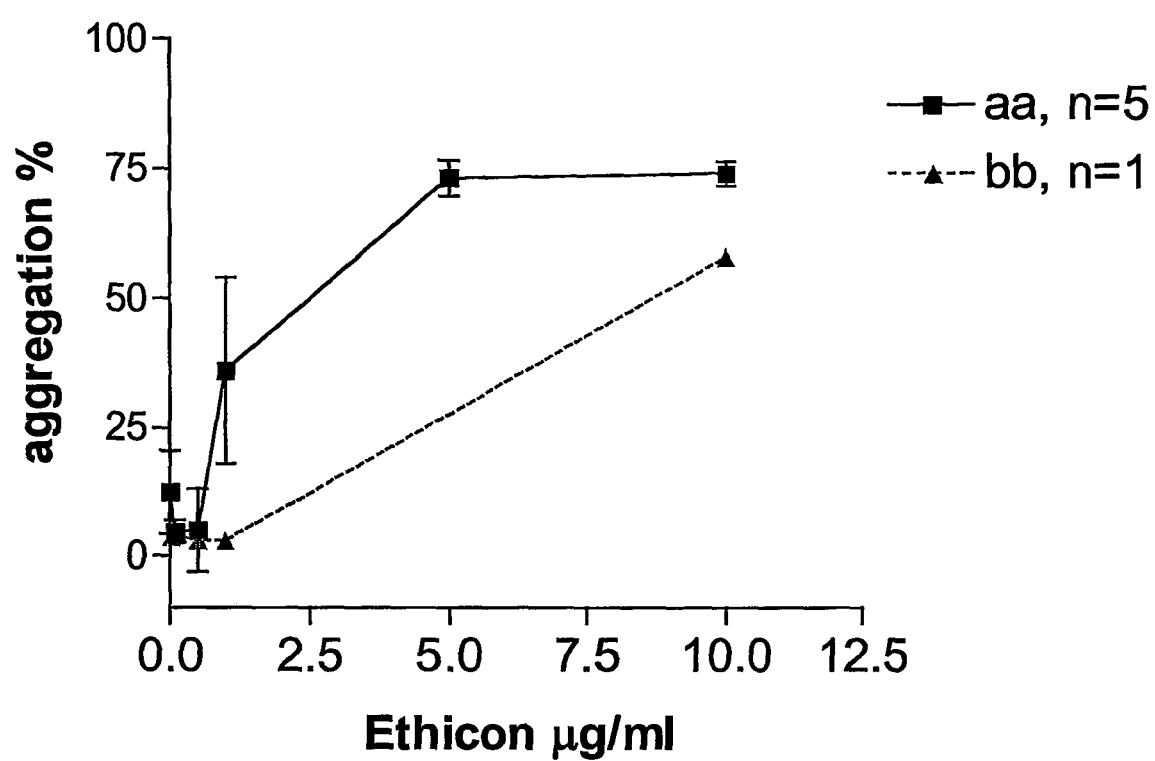
Figure 4C:
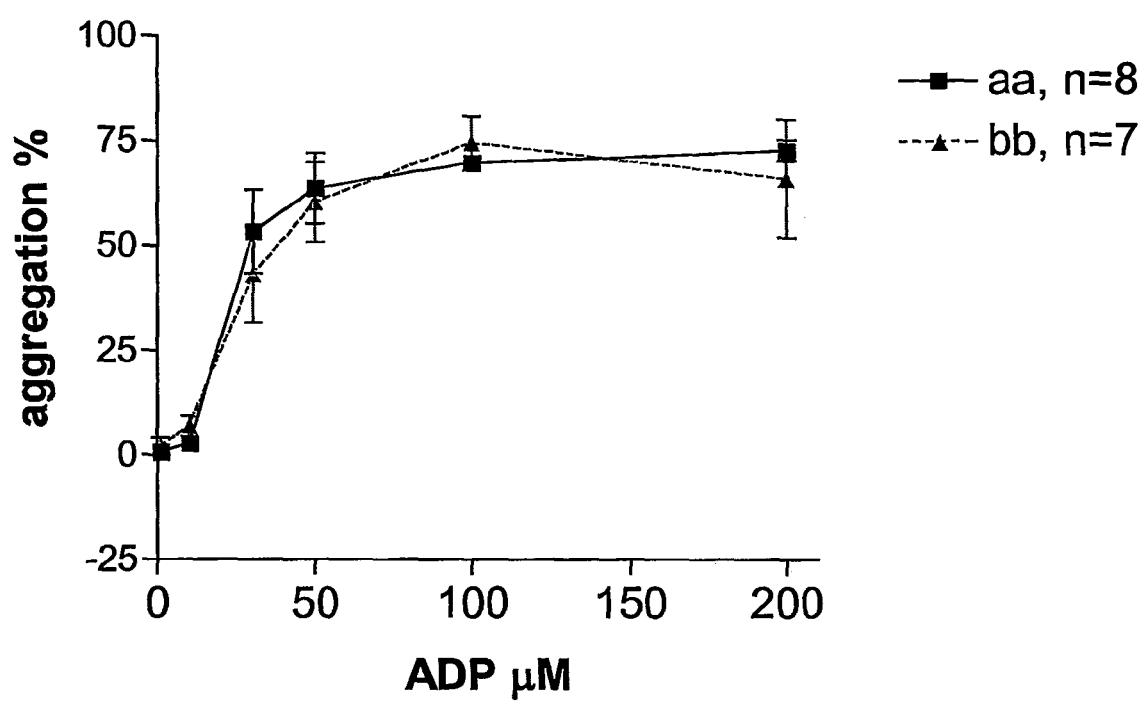
Figure 5A:
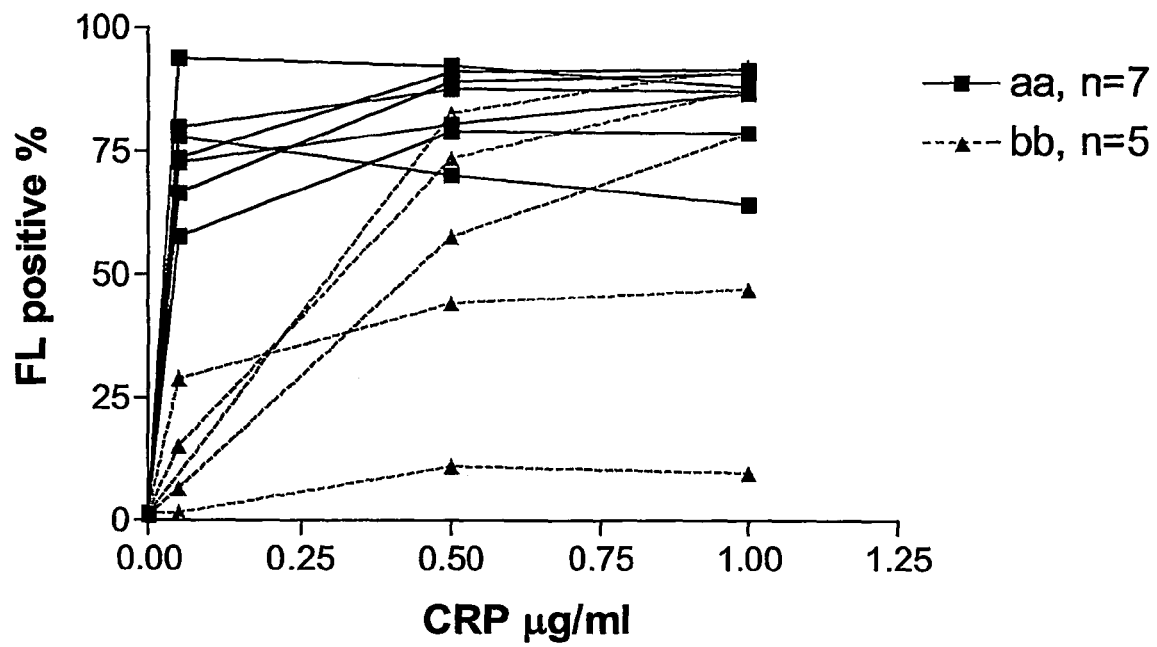
Figure 5A:
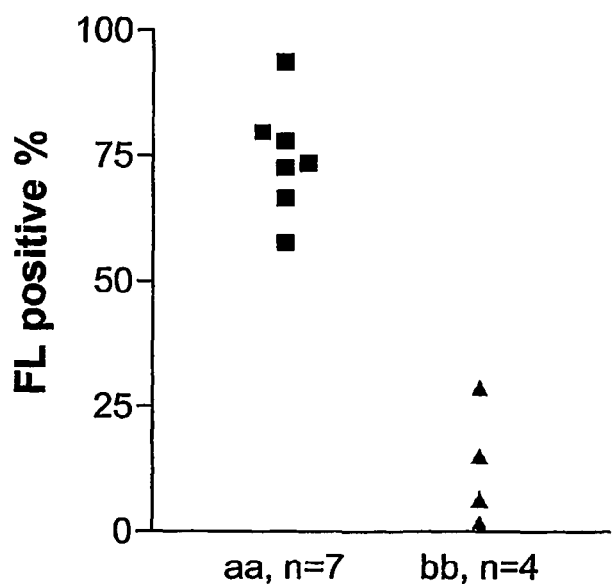
Figure 5B:
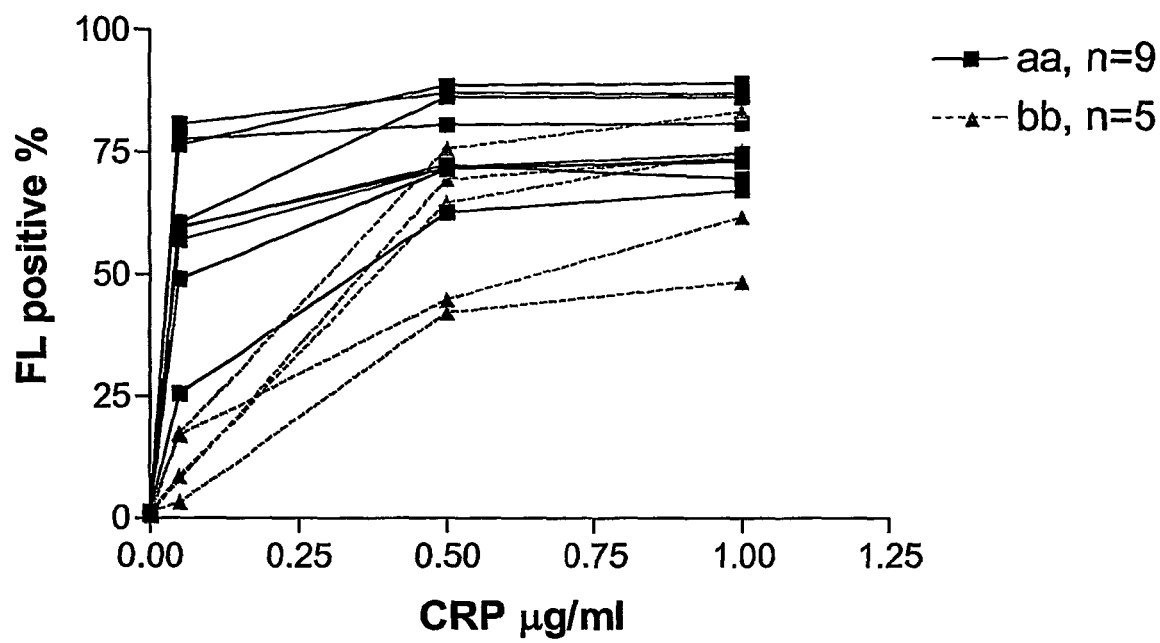
Figure 5B:
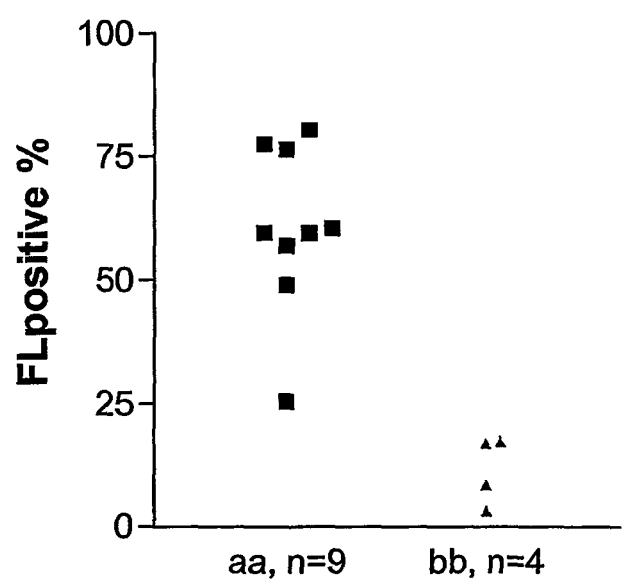
Figure 5C:
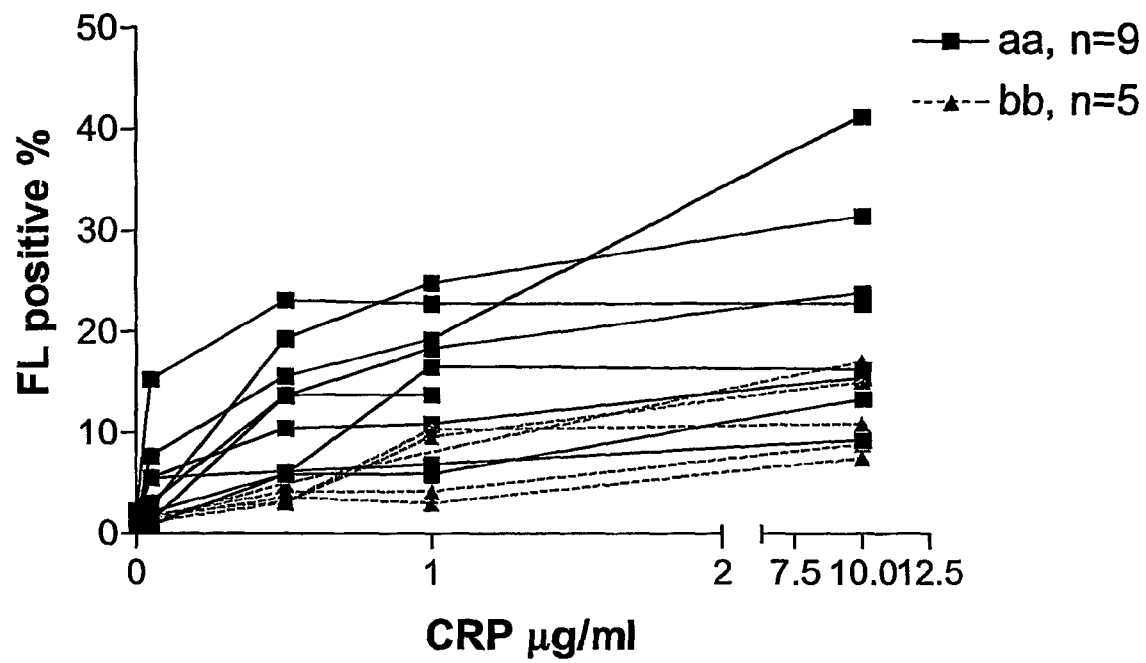
Figure 5C:
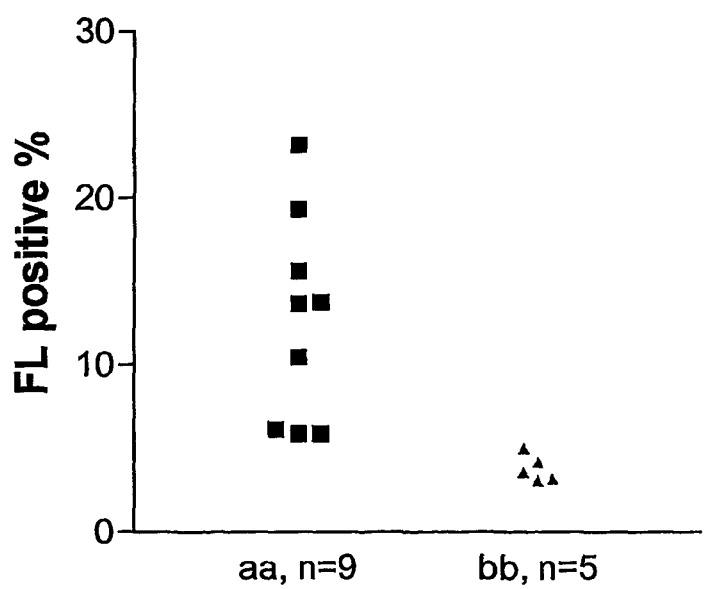

This pronounced difference was also observed with platelet aggregation responses stimulated with collagen type I (Ethicon; 5 'aa' donors and 1 'bb' donor studied; FIG. 4B). As expected there was no significant difference in the response to ADP (8 'aa' and 7 'bb' donors studied, FIG. 4C).

Differences Between the Two Alleles were Confirmed in Events Downstream of GPVI

Figure 6:
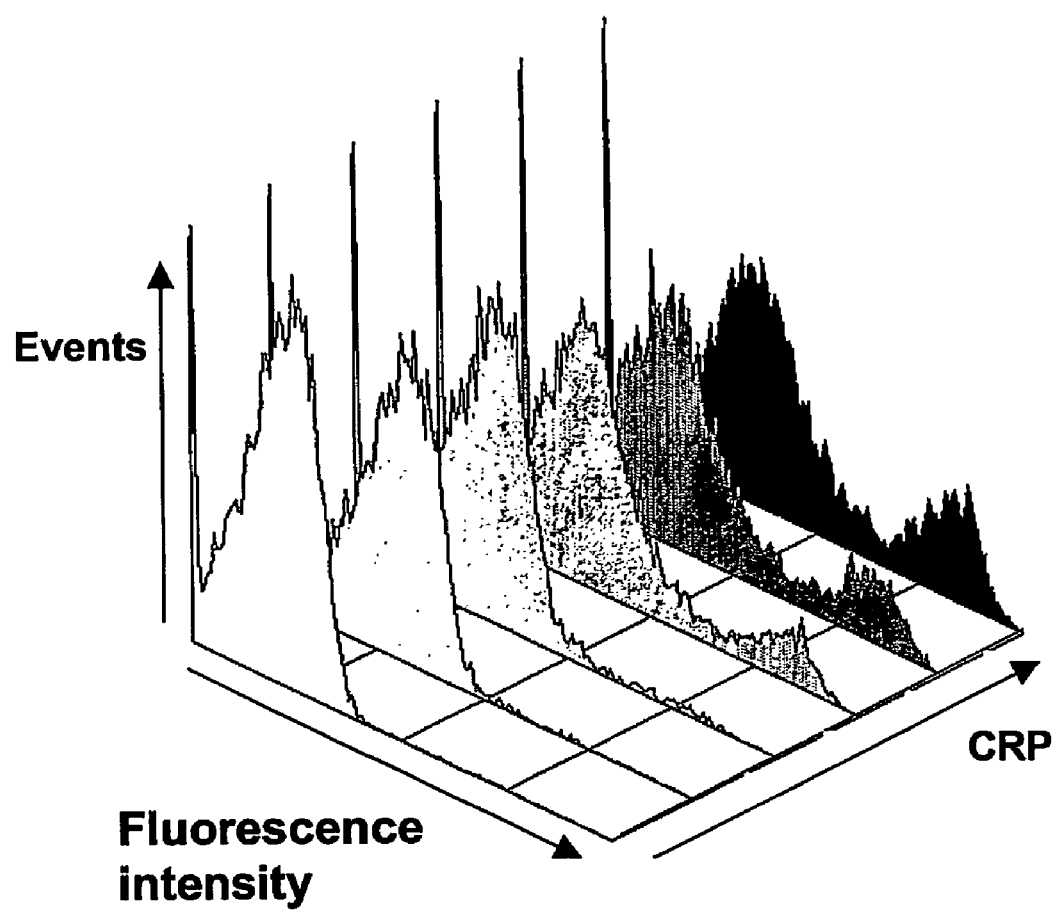

We investigated whether the profound difference in CRP responsiveness could also be observed in whole blood, by measuring the binding of fibrinogen and annexin V and the release of α granules as indicators of platelet activation. CRP was added to whole blood at 4 different concentrations and the activation markers were tested on CD61 positive events. For all three markers there was a clear dose-response relation (FIG. 5). The platelets from 'aa' individuals (n=7) bound more fibrinogen and more annexin V after stimulation with CRP (at 0.05 μg/ml and 0.5 μg/ml, respectively) than those from 'bb' donors (Mann-Whitney U test, for fibrinogen, p=0.0061; for annexin V, p=0.0010). Platelet degranulation as measured by the binding of the CD62P moAb after CRP stimulation at 0.05 μg/ml was also significantly different between the two groups (Mann-Whitney U test, p=0.0028). At CRP levels which gave maximal aggregation (10 μg/ml), only up to 10-30% of platelets bound annexin V, where as 70-90% of platelets were CD62P positive (FIG. 5). The annexin V positive platelet population comprised a distinct population of cells, increasing dose-dependently (FIG. 6).

The baseline levels for activation as determined by the three markers did not differ between the two groups (data not shown). The response to ADP was dose-dependent with all the activation markers, but there were no significant differences between the 'aa' and 'bb' samples (data not shown).

Materials and Methods

Samples

Samples were obtained from the static clinic of our blood centre which consists of donors who are regularly apheresed for procurement of platelet concentrates as well as whole blood donors. The apheresis donors are selected on ABO groups (mainly A and O) and on platelet counts (over 250× $10^9$/l). The study group consisted of 19 healthy blood donors (14 male, 5 female). For this study, 1153 donors were genotyped for the five replacement SNPs in the GPVI gene in order to identify adequate numbers of donors homozygous for each allele and to exclude individuals with rare GPVI alleles. Homozygotes for the high frequency allele (encoding SKTQH) (SEC) ID NO: 85) are labelled 'aa' and for the low frequency allele (encoding PEALN) (SEQ ID NO: 86) 'bb'. All experiments were performed on freshly drawn samples and when possible on paired ('aa' versus 'bb') samples. Samples of the 'aa' type were used as controls for calibration of the flow cytometry and platelet aggregation studies. In addition, 89 random blood donors were studied for the GPVI expression levels. The project has an approval from the local regional ethics committee, and is in accordance with the National Blood Service guidance for the use of donor blood for research. All the donors have consented. None of the volunteers had used aspirin in the 5 days preceding donation and sampling was by venepuncture of the antecubital vein with a 19 gauge needle.

Antibodies and other Reagents

The following monoclonal antibodies (moAb) were used for measuring GPVI and GPIaIIa expression: Single chain variable domain antibody fragments (scFvs) 1C3 and 10B12 against GPVI, scFv 2D4 (anti-HLA-A2, Watkins et al, personal communications), scFv Fog-1 (anti-D) and the murine moAbs NBS-P16 (CD49, anti-GPIaIIa), 9E10 (anti-myc tag). The binding of scFvs was as previously described in a three-step assay using moAb 9E10 and fluorescein isothiocyanate (FITC)-conjugated goat anti-mouse IgG (Dako, Cambridge, UK; Watkins et al, 2000) and the binding of the murine moAbs was by the classic two-step assay (von dem Borne et al, 1978). Expression of P selectin (CD62P) and phosphatidyl serine and the binding of fibrinogen was determined with FITC conjugated antibodies: anti-CD62P (Pharmingen, Becton Dickinson, San Diego, Calif.), annexin V (Molecular Probes, Eugene, Oreg.) and rabbit anti-human fibrinogen (Dako A/S, Denmark). Phycoerythrin (PE) labelled anti-CD61 (Pharmingen, Becton Dickinson, San Diego, Calif.) was used to gate for platelets. Collagen-related peptide (CRP), collagen as native type I fibers from bovine tendon (Ethicon Inc., Somerville, N.J.), adenosine diphosphate (ADP, Sigma, St. Louis, Mo.) as well as GPRP peptide (Gly-Pro-Arg-Pro (SEQ ID NO: 87), inhibitor of fibrin polymerization, Sigma Chemical Co, St Louis, Mo., USA) were used. All the buffers for the flow cytometry were 0.22 μm filtered.

Allele Discrimination for GPVI, GPIaIIa (α2 C-52T) and GPIbα (C-5T) Polymorphisms with TaqMan Allele discrimination for GPVI in 1153 donors will be described in detail by Watkins et al (manuscript in preparation). Genomic primers and probes for allelic discrimination by Taqman were designed using Primer Express (Perkin Elmer). Details of the primers and probes at which the assays were performed are as follows:

Borne et al, 1978). In short, platelet rich plasma (PRP) was prepared from EDTA-anticoagulated blood (stored at 4° C. overnight) by centrifugation at 1400 rpm for 10 min. The PRP was washed twice in PBS/EDTA/BSA buffer (phosphate-buffered saline, PBS with 10 mM EDTA, pH 6.8 and supplemented with 0.25% bovine serum albumin, BSA) by centrifugation at 3000 g for 6 min. Platelet count was adjusted to $1 \times 10^7$/ml (counted by Sysmex K1000, Milton Keynes, UK), and PRP containing $5 \times 10^5$ platelets was transferred into polystyrene tubes (for the flow cytometry, LIP Ltd) containing 150 μl purified monoclonal scFv or antibody. When studying 89 donor samples separately, the assay was performed using 96-well microtiter plates (Dynex Technologies, Chantilly, Va.). The antibodies were used at saturating concentrations: scFv 1C3 at 10 (or 20) μg/ml, scFv 10B12 at 50 μg/ml, scFv 2D4 at 20 μg/ml and moAb NBS-P16 at 1 μg/ml, moAb 9E10 at 30 μg/ml. After incubation for 1 h at room temperature (RT), the platelets were washed with 3 ml buffer, and resuspended in 100 μl 9E10 moAb (at 30 μg/ml) and incubated for 1 h at RT. The platelets were then washed once, resuspended in 50 μl of a 1:20 dilution of FITC-conjugated goat anti-mouse IgG (Dako, Cambridge, UK) and incubated for 30 min at RT in the dark. After a final wash, platelets were resus-

| | Taqman primers | |
|---|---|---|
| Variant | Sense (5'---3') (SEQ ID NO:) | Antisense (SEQ ID NO:) |
| GpVI T655C (S219P) | TCCCAGGAACCTCTGTGACC (5) | CTCATACGCTGTGCACCAGAA (13) |
| GpVI A709G (K237E) | CTCAGAAGCCACCGCTGAA (6) | CTGAGCATGAAATGCCTGGTT (14) |
| GpVI A745G (T249A) | TTTCACACTTAGCCTTTGTTTGGTT (7) | CCAGCTGGAGAGTCTGACTCCTT (15) |
| GpVI A950T (Q317L) | AAGCGCCTGCGGCAC (8) | ACATAACCCGCGGCTGTG (16) |
| GpVI C964A (H322N) | AGGAAGCGCCTGCGG (9) | TCCCATGCCATGATCCCT (17) |
| GpVI -C154T | TCCTTGGAGCTTGTGTGCAA (10) | CGGCCTTCCTAATTGAGACTCAT (18) |
| GpIbα -T5C | GGATCCACTCAAGGCTCCCT (11) | GGAGCAGCAAGAGGAGGAGA (19) |
| GpIa -C52T | CCGGTGTTTGCGGAATCA (12) | CCGGTGAGAGCAGGGAAAA (20) |

| | Taqman probes | |
|---|---|---|
| Variant | FAM Probe (5'---3') (SEQ ID NO:) | VICProbe (5'---3') (SEQ ID NO:) |
| GpVI T655C | AGAACCACCTTCCTCGGTAGCAGGTAG (21) | ACCACCTTCCCCGGTAGCAGGT (29) |
| GpVI A709G | TCACAAACAAAGTCTT (22) | CACAAACGAAGTCT (30) |
| GpVI A745G | TTCTAGGAGTATCACCACCAGT (23) | CTAGGAGTATCACCGCCAGT (31) |
| GpVI A950T | CCTCCCGCAGACCCGGAAA (24) | CCTCCCGCTGACCCGGAAA (32) |
| GpVI C964A | CTGACCCCCGTGTGATTTCCG (25) | TCCTGACCCCCGTTTGATTTCC (33) |
| GpVI -C154T | CGTAGCCGGCTCCT (26) | CCGTAGCCAGCTCC (34) |
| GpIbα -T5C | CACAGGTCCTCATGCC (27) | ACAGGCCCTCATGCC (35) |
| GpIa -C52T | CCGCCCCGGCCCG (28) | CGCCCCAGCCCGC (36) |

A total of 8 assays were developed, 3 using standard probes and 5 using MGB probes. Probes specific for the wild-type allele (A2) were labelled with FAM and the mutant allele (A1) with VIC.

DNA samples of the 1153 donors were genotyped for all GPVI SNPs. Allelic discrimination assays were performed in a total volume of 15 μl with 900 nM each primer, 200 nM each probe and 5 μl of genomic DNA. Amplification reactions were performed following standard conditions with an annealing temperatures of 60° C. Allelic discrimination was determined using a post-PCR plate reader on a PE 7700 (Perlin Elmer) and the alleles were assigned using the auto-calling software. The raw data and allele assignments were exported as an Excel spreadsheet.

Flow Cytometry for GPVI Platelet Surface Expression

Samples were tested for platelet surface expression level of GPVI by the platelet immunofluorescence test (von dem pended in 200 μl buffer and the fluorescence intensities of 10,000 events were analysed using a flow cytometer (Coulter X L, Luton, U K). The median fluorescence intensity (FL) for green fluorescence, FL1, was recorded on a logarithmic scale from 0.1 to 1000. The relative FL for each sample was obtained by dividing the median FL by that of the negative control (9E10) of each sample.

Platelet Aggregation

PRP was obtained from fresh citrated (final concentration 0.38 tri-sodium citrate) whole blood by centrifuging at 1200 rpm for 12 minutes. Platelet-poor plasma (PPP) was prepared from PRP by centrifugation at 7000 rpm for 10 minutes. The platelet count was then adjusted to $200 \times 10^9$/l with PPP. To determine platelet aggregation, light transmission in PRP (250 μl) was measured and recorded on a PAP-4 four channel aggregometer (Bio/Data Corporation, Horsham, Pa., USA) at 37° C. over 10 min. The results were expressed as arbitrary units with 100% transmission (corresponding to 100% aggregation) set using PPP. Platelet aggregation was induced by addition of either CRP at concentrations between 0.05 and 2.0 µg/ml, collagen as native type I fibers from bovine tendon at 0.1 to 10.0 µg/ml and ADP at 1.0 to 20 µM.

Platelet Activation in Whole Blood Using Flow Cytometry

Whole blood flow cytometry was used to detect platelet activation by CRP and ADP. Citrate-anticoagulated whole blood (5 µl) was added to Hepes buffered saline (HBS buffer, 0.145M NaCl, 5 mM KCl, 1 mM MgSO4, 10 mM Hepes at pH 7.4, final volume 70 µl) containing PE-labelled anti-CD61, agonist (CRP or ADP) and FITC-labelled activation marker. CRP was tested at concentrations between 0.05 to 10 µg/ml and ADP at 1, 10 and 100 µM. We used the following activation markers: anti-fibrinogen (2 µl/test), anti-CD62P (P-selectin, 10 µl/test) and annexin V (5 µl/test). After the incubation for 20 min at RT, the cells were fixed with 200 µl of 0.2% formaldehyde (37-41% formaldehyde solution, BDH Laboratory Supplies, Poole, UK) in 0.9% NaCl for 10 min. When using annexin V as the activation marker, the HBS contained 1 mM CaCl2 and GPRP and the samples were not fixed. The samples were freshly analysed with a flow cytometer (Coulter X L, Luton, U K) using a "live platelet gate" set on the basis of forward and side light scatter profiles. In the analysis, only FL2 positive events (i.e. CD61 positive ones) were analysed for an FL1 signal, and data from 5000-10000 events per sample was collected. The median FL1 of each activation marker for unstimulated platelets was recorded in order to compare the baseline activation level between different donors. Furthermore, the analysis was carried out with software Expo32 (Applied Cytometry Systems, Sheffield, UK). The threshold for positive events was set by adjusting a marker on non-stimulated platelets stained with the activation marker, so that less than 1% were above the level on the FL1 histogram. Since bound fibrinogen, P-selectin and annexin V are present at low levels on non-stimulated platelets, the data were expressed as the % FL1 positive platelets.

Statistical Analysis

Arithmetic mean, median, standard deviation (SD), range and 95% confidence interval (CI 95%) were calculated, for the most variables. The statistical analysis was performed using GraphPad Prism version 3.0a (GraphPad Software, San Diego, Calif.).

Discussion

Collagen mediated signalling of platelets is via GPVI, the absence of which is associated with a mild bleeding phenotype and a strongly reduced response to collagen and no response to CRP in vitro (Moroi et al, 1989). CRP binding to GPVI is dependent on the presence of the GPO repeat motif (Knight et al, 1999), and activation of platelets evokes tyrosine phosphorylation of an immunoreceptor tyrosine-based activation motif (ITAM) by a Src family kinase (Watson et al, 2001).

We observed significant inter-individual variation in the response of human platelets to CRP in aggregation and in whole blood platelet activation assays. We observed significant differences in thrombin generation. There are two major GPVI alleles which differ by five amino acid replacements, three in the stem (S219P, K237E, T249A) and two in the cytoplasmic domain (Q317L and H322N). We hypothesised that functional differences may be related to the presence of these different GPVI alleles. There are several reasons why this might be the case. First, when testing the binding of our anti-GPVI scFv 1C3 to platelets from 89 random donors we observed a relative low level of expression on the platelets of the single sample which was homozygous for the low frequency allele (FIG. 1A). Second, we observed a trend for lower 1C3 binding in the 'ab' donors when compared with 'aa' homozygotes (FIG. 1B). Third, one of the two mutation in the proline rich cytoplasmic domain (RPLPPLPPLPQT) (SEQ ID NO: 88) replaces a neutral Q297 with a positive charged lysine. The PLPPLPPLP (SEQ ID NO: 89) motif is a target of that for the SH3 domain of the Src family kinases (Rickles et al, 1994) indicating that such signalling proteins may dock in this region of GPVI (Watson et al, 2001). Finally, it is likely that GPVI dimerisation occurs upon ligand binding and the kinetics of this process may depend on the sequence of the stem and possibly the cytoplasmic domain. To test our hypothesis we genotyped 1153 volunteers for the 5 relevant GPVI SNPs. The resulted in the identification of 745 (65.4% homozygotes for the high frequency allele, 28 (2%) for the low frequency one, 290 heterozygotes and the remainder 80 were examples of 'rare' hybrid allleles. We used the platelets of 12 and 8 'a' and 'b' homozygotes for functional studies.

We showed significantly higher binding of both GPVI specific scFvs to the platelets of the 'aa' homozygotes when compared with the 'bb' group. It is highly unlikely that the observed difference in binding is the result of linked mutations in the GPVI gene segment encoding the antibody binding sites. Both antibodies 1C3 and 10B12 bind to the C2-like ectodomains (residues 1-185) and no replacement mutations were observed in these domains in the donors used for this study. Binding studies of monoclonal GPVI antibodies to human platelets of different individuals has only been performed by one other group (Chen et al, 2002). Using the platelets from 20 individuals they estimated an average copy number to approximately 1200 molecules per platelet with a tightly regulated expression and that was independent of GPIaIIa density. It is unlikely that an individual homozygous for the low frequency 'bb' allele was part of the study. Others used the lectin-like snake venom convulxin (CVX) as a semi-quantitative molecular probe to study total platelet GPVI content and to study the relation between GPVI content and function (Furihata et al, 2001). In a limited sample size of 23 individuals, they showed a positive correlation between CVX-induced platelet pro-coagulant activity and total GPVI content. No differences were found in CVX-induced platelet aggregation or platelet adhesion to CVX. Their study suggests a five-fold variation in GPVI content which was associated with the expression level of GPIaIa. With our GPVI antibody we only observed a 2-3 fold difference of membrane expression of GPVI. There are several reasons for the discrepancies between the two studies. First, the sample size was too small to include homozygotes for the 'low frequency ' 'b' allele and no significant difference between 'aa' and 'ab' was observed. Second, the relation between surface and total expression of GPVI is not known. Thirdly, the possible limited specificity of CVX may also influence the results of the functional studies. Finally, only a limited analysis was performed on the genetic variability in the GPVI gene of the 23 individuals.

The dose-response studies with CRP show a significant split between the individuals homozygous for the 'a' or 'b' allele. This difference was also observed with collagen type I (ethicon) in aggregation indicating that the co-operation of GPIaIIa and GPVI did not grossly alter the magnitude of aggregation. A careful analysis of the aggregation responses on ethicon in the homozygous 'a' donors either on basis of the C-52T SNP in the GPIa gene or on basis of moAb NBS-P16 binding did not reveal an independent effect. It is unclear why we were unable to observe an effect of the GPIa SNP which was initially reported by Kunicki et al (1993) in aggregation studies and confirmed by us in whole blood flow studies at high shear rate (Roest et al, 2000). There are several possible explanations for this observation.

First, the effect of the GPVI SNPs is so profound that the more modest effect of the GPIa SNP is not obvious. Moreover, in our series the link between the GPIa SNP and level of expression was less clear (FIG. 3). We considered whether the poor correlation between the GPIa alleles and expression was resulting from us having used another CD49b moAb but the seems unlikely as the variation of GPIaIIa expression observed is not dissimilar to that observed by others. Second the GPIa and GPVI SNPs may be in linkage disequilibrium. We tested this on the data obtained from 600+DNA samples and were unable to obtain evidence for such a linkage (data not shown). The absence of linkage is not surprising as the GPIa and GPVI genes are on chromosomes 5 and 19, respectively. Third, it may be the type of collagen used and its purity and composition differed. Finally, our donors were selected on basis of their GPVI allele status, and in this group there was only one donor homozygous—52TT for the GPIa, SNP linked to low expression (Table 1). A close inspection of published results revealed that the functional difference between the two GPIa genotypes is rather small, especially when using collagen type I or m (also they used genotyping according to the GPIa C807T polymorphism site, and combined the data on C vs T allele). We therefore assume that the latter together with the dramatic effect of the GPVI alleles are most likely, although not proven, explanation for the non-penetrance of the GPIa-SNP.

Interestingly, within the group of 'aa' donors there is a reasonably wide variation in GPVI antibody binding. With the platelets of two of the eight 'aa' donors, the mean fluorescence values were obtained within the average+1 SD of the group of 'bb' platelets. Despite their reduced surface expression, these two donors demonstrated a typical 'aa' phenotype, showing significant difference to 'bb' group. This led us to conclude that the observed difference in CRP response is not solely determined by a difference in membrane expression of GPVI. It is likely, that the difference is the result of i) an altered kinetics of dimerisation of GPVI, ii) a reduced ability of GPVI of the 'b' type to accrue the required cytosolic molecular complex for signalling, possibly because of the replacement of the non-charged glutamine by the positively charged lysine. Of course, GPVI membrane density may also contribute to the former.

As expected, the difference between the two groups in their reactivity towards CRP was confirmed when events downstream of GPVI mediated signalling were measured. In these experiments activation of platelets was achieved by adding CRP to whole blood and the binding of fibrinogen and of annexin V and the extent of a granule release were measured after minimal manipulation of the sample. As reported, there is a clear uncoupling between the α granule release and annexin V binding (Dale et al, 2002). Here, we showed that at CRP levels of 10 μg/ml, renders 70-90% of platelets positive for CD62P whereas only 10-30% of platelets are positive with annexin V, the marker for exposure of anionic phospholipids (i.e. loss of membrane asymmetry) and prerequisite for procoagulant activity of platelets. The question whether the change in the phospholipid composition of the membrane was the direct or indirect consequence of GPVI signalling is not answered by our study. The time course measurement of the generation of thrombin showed a strong linkage between the time of first thrombin generation and the GPVI genotype.

Croft et al (2001) found that the 'bb' type (homozygous for 219PP) to be a risk factor for cardiovascular disease, only after sub-grouping the patient population. However, it is interesting that they stated the 'bb' type being the risk factor for arterial thrombosis, although we find that to be the less-responsive, i.e. EB or bleeder phenotype. We found with CRP-induced platelet aggregation and activation, clear differences between the two groups. No differences were seen with other agonists, such as ADP, indicating that the functional differences seen are GPVI-mediated. Whether the possible GPVI expression variation between individuals and the observed in vitro functional differences in platelet activation are of pathological significance is not yet known.

The data presented in Example 1, and shown in FIGS. 9-12 has been further expanded upon, and is presented in Example 2.

REFERENCES

Chen H, Locke D, Liu Y, Liu C, Kahn M. The platelet receptor GPVI mediates both adhesion and signaling responses to collagen in a receptor density-dependent fashion. J Biol. Chem. 2002; 277:301.

Clemetson J M, Polgar J, Magnenat E, Wells T N, Clemetson K J. The platelet collagen receptor glycoprotein VI is a member of the immunoglobulin superfamily closely related to FcalphaR and the natural killer receptors. J Biol. Chem. 1999; 274:29019-24.

Croft S A, Samani N J, Teare M D et al. Novel platelet membrane glycoprotein VI dimorphism is a risk factor for myocardial infarction. Circulation. 2001; 104:1459.

Dale G L, Friese P, Batar P et al. Stimulated platelets use serotonin to enhance their retention of procoagulant proteins on the cell surface. Nature 2002; 415:175-9.

Di Paola J, Federici A B, Mannucci P M et al. Low platelet α2β1 levels in type I von Willebrand disease correlate with impaired platelet function in a high shear streess system. Blood. 1999; 93:3578.

Furihata K, Clemetson K J, Deguchi H, Kunicki T J. Variation in human platelet glycoprotein VI content modulates glycoprotein VI-specific prothrombinase activity. Arterioscler Thromb Vasc Biol. 2001; 21:1857.

Gachet C. ADP receptors of platelets and their inhibition. Thromb Haemost 2001; 86:222-32.

Goodall A H. Platelet activation during preparation and storage of concentrates: detection by flow cytometry. Blood Coagulation and Fibrinolysis. 1991; 2:377.

Kehrel B, Wierwille S, Clemetson K J et al. Glycoprotein VI is a major collagen receptor for platelet activation: it recognizes the platelet-activating quaternary structure of collagen, whereas CD36, glycoprotein IIb/IIIa, and von Willebrand factor do not. Blood. 1998; 91:491-9.

Knight C G, Morton L F, Onley D J, Peachey A R, Ichinohe T, Okuma M, Farndale R W, Barnes M J. Collagen-platelet interaction: Gly-Pro-Hyp is uniquely specific for platelet Gp VI and mediates platelet activation by collagen. Cardiovasc Res. 1999; 41:450-7.

Kritzik M, Savage B, Nugent D J, Santoso S, Ruggeri Z M, Kunicki T J. Nucleotide polymorphisms in the a2 gene define multiple alleles that are associated with differences in platelet α2β1 density. Blood. 1998; 92:2382.

Kunicki T J, Orchekowski R, Annis D S, Honda Y. Variabilty of integrin alpha 2 beta 1 activity on human platelets. Blood. 1993; 82:2693.

Kunicki T J, Kritzik M, Annis D S, Nugent D J. Hereditary variation in platelet integrin α2β1 density is associated with two silent polymorphisms in the α2 gene coding sequence. Blood. 1997; 89:1939.

Jacquelin B, Rozenshteyn D, Kanaji S, Koziol J A, Nurden A T, Kunicki T J. Characterization of inherited differences in transcription of the human integrin a2 gene. J Biol. Chem. 2001; 276:23518.

Jacquelin B, Tarantino M D, Kritzik M et al. Allele-dependent transcriptional regulation of the human integrin a2 gene. Blood. 2001; 97:1721.

Metcalfe P, Williamson L M, Reutelingsperger C P M, Swann L Ouwehand W H, Goodall A H. Activation during preparation of therapeutic platelets affects deterioration during storage: a comparative flow cytometric study of different production methods. Br J Haematol. 1997; 98:86.

Moroi M, Jung S M, Okuma M, Shinmyozu K. A patient with platelets deficient in glycoprotein VI that lack both collagen-induced aggregation and adhesion. J Clin Invest. 1989; 84:1440.

Rickles R J, Botfield M C, Weng Z et al. Identification of Src, Fyn, Lyn, P13K and Abl SH3 domain ligans using phage display libraries. EMBO J. 1994; 13:5598-604.

Roest M, Sixma J J, Wu Y-P et al. Platelet adhesion to collagen in healthy volunteers is influenced by variation of both a2 µl density and von Willebrand factor. Blood. 2000; 96:1433.

Santoso S, Kunicki T J, Kroll H, Haberbosch W, Gardemann A. Association of the platelet glycoprotein Ia C807T gene polymorphism with nonfatal myocardial infarction in younger patients. Blood. 1999; 93:2449.

von dem Borne A E, Verheugt F W, Oosterhof F, von Riesz E, de la Riviere A B, Engelfriet C P. A simple immunofluorescence test for the detection of platelet antibodies. Br J Haematol. 1978; 39:195-207.

Watkins N A, Brown C, Hurd C, Navarrete C, Ouwehand W H. The isolation and characterisation of human monoclonal HLA-A2 antibodies from an immune V gene phage display library. Tissue Antigens 2000; 55:219-28.

Watson S P, Asazuma N, Atkinson B et al. The role of ITAM- and ITIM-coupled receptors in platelet activation by collagen. Thromb Haemost 2001; 86; 276-88.

TABLE I

Twelve 'aa' (SS219, KK237, TT249, QQ317, HH322) and 7 'bb' (219PP, 237EE, 249AA, 317LL, 322NN) donors were tested for three other single nucleotide polymorphisms.

| Donor | GPVI 219, 237, 249, 317, 322 | | GPIbα T-154C | GPIa T-5C | C-52T |
|---|---|---|---|---|---|
| 1 | SKTQH | (SEQ ID NO: 85) | CT | TT | CT |
| 2 | SKTQH | (SEQ ID NO: 85) | TT | TT | CC |
| 3 | SKTQH | (SEQ ID NO: 85) | TT | TT | CC |
| 4 | SKTQH | (SEQ ID NO: 85) | CT | TT | CT |
| 5 | SKTQH | (SEQ ID NO: 85) | CT | TT | CT |
| 6 | SKTQH | (SEQ ID NO: 85) | CC | TT | CT |
| 7 | SKTQH | (SEQ ID NO: 85) | CT | TC | CC |
| 8 | SKTQH | (SEQ ID NO: 85) | CT | TT | CC |
| 9 | SKTQH | (SEQ ID NO: 85) | CT | TT | CC |
| 10 | SKTQH | (SEQ ID NO: 85) | TT | TT | CT |
| 11 | SKTQH | (SEQ ID NO: 85) | CT | TC | CC |
| 12 | SKTQH | (SEQ ID NO: 85) | TT | TT | CT |
| 13 | PEALN | (SEQ ID NO: 86) | CC | TT | CT |
| 14 | PEALN | (SEQ ID NO: 86) | CC | CC | CC |
| 15 | PEALN | (SEQ ID NO: 86) | CC | TT | CC |
| 16 | PEALN | (SEQ ID NO: 86) | CC | TC | TT |
| 17 | PEALN | (SEQ ID NO: 86) | CC | TT | CT |
| 18 | PEALN | (SEQ ID NO: 86) | CC | TC | CT |
| 19 | PEALN | (SEQ ID NO: 86) | CC | TT | CT |

EXAMPLE 2

Sequence Polymorphisms at the Human Glycoprotein VI Gene Reveals Conserved Immunoglobulin Domains, but Highly Polymorphic Stem and Cytoplasmic Domains The promoter, exons and flanking intron sequences of human GP6 gene were re-sequenced in a "core" panel of 94 Caucasians. Eighteen variable sites were identified that segregated as 37 haplotypes with frequencies between 0.195 to 0.003. All the variable sites were single nucleotide polymorphisms (SNPs), six of which encoded amino acid substitutions in GP6. However, only one of these (C307G), encoding a Leu83Val substitution with a frequency of 0.005, was in the immunoglobulin-like, ligand binding domains of GP6. A high-resolution SNP map of GP6 by exon re-sequencing in 188 Caucasoid chromosomes (94 individuals) identified a total of 18 SNPs, 6 of which encoded for amino acid substitutions. Analysis revealed that the 18 variable sites segregated into 37 haplotypes and that none of them deviated significantly from the Hardy-Weinberg equilibrium. When analysed in the absence of the C307G SNP, the non-synonymous SNPs segregated into 5 haplotypes, with the two most common haplotypes having frequencies of 0.79 and 0.18 in the core panel. Differences in GP6 specific responses to CRP or collagen of individuals homozygous for these two haplotypes have been observed and genetic variation at the GP6 locus has been linked to myocardial infarction. We therefore extended our study to an additional 1310 individuals (1127 Caucasians, 63 Koreans, 40 South African blacks, 40 Ethiopians and 40 Curaco) to fully characterise variation in GP6. All 5 sites were polymorphic in the populations studied and a total of 12 GP6 haplotypes were identified in the combined population. The Ethiopian and South African Black samples showed the most haplotype diversity.

The frequencies of the 5 common non-synonymous SNPs, which were in significant linkage disequilibrium (LD), were then determined in a panel 1127 Caucasians to fully characterise the GP6 isoforms present in the Caucasian population. This typing revealed that the 5 non-synonymous SNPs segregated into 8 haplotypes in Caucasians. In addition, despite the significant LD between the 5 SNPs, in 6.9% of individuals the complete GP6 genotype was not predicted by genotyping at a single variable site.

The study was then extended to samples from individuals of different ethnic origin. We genotyped for the 5 non-synonymous SNPs in samples from 63 Koreans, 40 South African blacks, 40 Ethiopians and 40 Curcoa. This genotyping revealed the presence of 4 additional GP6 haplotypes.

Materials and Methods

Population Samples

Two panels of Caucasoid donor DNA were established for this work. The sequencing panel (SP), consisting of DNA from 94 apheresis donors, was used to identify polymorphisms in the GP6 exons (plus flanking intron sequences) by direct sequencing of PCR products. Panel 1 was composed of 1127 DNA samples from donors and was used to determine the frequency of the 6 non-synonymous SNPs found at the GP6 locus. The only selection criterion for both panels was a platelet count >150×10$^9$/L. All samples were obtained with informed consent and with the approval of the National Blood Service internal review panel. Ethnic DNA samples were a kind gift from Dr Peter Forster (Department of Archaeology, University of Cambridge) and Dr Ellen van der Schoot (University of Amsterdam).

Isolation of Genomic DNA (gDNA)

gDNA was prepared from EDTA-anticoagulated blood samples using the Promega Wizard Genomic DNA isolation kit following the manufacturers' instructions (Promega, Southampton, UK). All GDNA samples were stored at −40° C. in distilled water. For genotyping and PCR, aliquots of GDNA (4 ng/μl) were dispensed into 96 well master plates and stored at 4° C.

Amplification of GP6 Exons

Oligonucleotides were designed to amplify exons 1 to 8 of GP6 in a total of 6 fragments as (Table 2). The primers were designed to be at least 50 to 100 bp from the end of the exons to allow the identification splice donor and acceptor site variants. Amplification reactions contained 25 mM MgCl$_2$, 20 mM each primer, 2 mM dNTPs, 0.6 U Hot-Start Taq polymerase (Qiagen, Crawley UK) and 20 ng of gDNA in a total volume of 30 μl. Amplification was performed over 40 cycles consisting of 1 min at 95° C., 1 min annealing and 1 min at 72° C. using a "touchdown" program. This consisted of 15 cycles during which the annealing temperature was reduced by 1° C. per cycle from 70° C. to 55° C. followed by 25 cycles with an annealing temperature of 55° C. All PCR reactions were performed on a GeneAmp 9700 PCR machine (Applied Biosystems, Warrington, UK).

After amplification, the products were purified using a QiaQuick PCR clean up kit following the manufacturers' instructions (Qiagen). Purified PCR products were eluted into 25 μl of distilled water and 1 μl analysed on a 1.5% agarose gel containing 1% (w/v) ethidium bromide. DNA quantification was performed by comparing the intensity of the purified sample with one of known concentration. The purified PCR products were then diluted to a concentration of 10 μg/ml for sequencing which was performed using BigDye v1.0 (Applied Biosystems) and an ABI373XL genetic analyser (Applied Biosystems).

Taqman Allelic Discrimination Assay

A total of 18 SNPs were identified following the sequencing of GP6 in the 94 samples. Taqman allelic discrimination assays were then designed for 9 of these 18 using Primer Express (Applied Biosystems). For three SNPs standard probes were used and for the remaining 5 MGB probes were used (Table 3). Allelic discrimination assays were performed in a total volume of 15 μl with 900 nM each primer, 200 nM each probe and 20 ng of GDNA. Amplification reactions were performed following standard conditions with annealing temperatures as detailed in Table 3. Where possible, control samples consisting of gDNA from homozygous and heterozygous donors was used. Allelic discrimination was determined using a post-PCR plate read on a PE 7700 (Perkin Elmer). The raw data and allele assignments were merged into the donor database for analysis.

Confirmatory Genotyping by Restriction Fragment Length Polymorphism (RFLP)

Confirmation of the presence of the novel SNP encoding for a Leu83Val substitution in GP6 identified in the heterozygous state in a single Panel 1 sample was obtained by developing a restriction fragment length polymorphism (RFLP) assay. The C307G (C6080G) SNP introduces a BstN1 restriction site into the low frequency 307G allele (Val encoding). A 279 bp fragment containing the C307G polymorphism was obtained by PCR amplification of gDNA using the oligonucleotide primers 5'-GGCCATGAAGAGAAGTCTGG-3' (SEQ ID NO: 37) and 5'-AGCAAGACCCTGTGTCCAAA-3' (SEQ ID NO: 38). Amplification was performed in a total volume of 50 μl containing 5 μl genomic DNA (4 ng/μl), 7.5 μl 10×PCR buffer, 1.5 μl MgCl$_2$, 15 mM each dNTPs, 12 μM each primer and 0.3 U of Taq DNA polymerase. Thermocycling conditions were as for amplification of GP6 exons. 20 μl of the PCR product was then digested with 1 U BstN1 (New England BioLabs) for 120 minutes at 60° C. and then analyzed on a 2% agarose gel containing 1% (w/v) ethidium bromide.

Haplotype Inference and Statistical Analysis

Haplotypes in the genotyped samples were determined by using either Clarks algorithm (Clark, 1990) or the EM algorithm implemented using Arlequin. The parameter FST was used to measure variation between populations.

Results

Polymorphic Variation Identified at GP6 by Re-Sequencing

A complete analysis of the sequences of the PCR products obtained from the 94 samples identified 18 SNPs in the GP6 exon and promoter sequence analysed (Table 4). These 18 included the 9 SNPs already present in GenBank and 9 novel SNPs. In general, the SNPs were distributed evenly throughout the GP6 cDNA sequence, but, with the exception of the C307G polymorphism, only silent mutations were found in the Ig-like domains of GP6 (FIG. 12). Eight of the novel SNPs were silent and one (C307G) encoded an amino acid replacement of Leucine for Valine at position 83 in the first Ig-like domain of GP6. The C307G polymorphism was confirmed by RFLP in all positive samples (Data not shown).

Taqman allelic discrimination assays were developed for 9 of the SNPs as described (Table 3) and these were used to genotype the sequencing panel samples. We observed complete concordance between the genotypes as determined by gDNA sequencing and by Taqman (Data not shown). The 9 Taqman assays were next used to genotype the 1 127 panel 1 samples (Table 4). In all instances, no significant differences between the allele frequencies in the two panels was observed for any SNP (Table 4). None of the variant sites showed deviation from the Hardy-Weinberg equilibrium in either the sequencing panel or Panel 1 (Data not shown).

Haplotype Variation and Linkage Disequilibrium in GP6 in the Sequencing Panel

Sequence haplotype relationships amongst the 18 SNPs in the sequencing panel were determined using Clarks and the EM algorithms. In total, 37 haplotypes were observed in the 188 chromosomes identified in the GP6 gene (Table 5). Analysis of linkage between the 18 SNPs in the sequencing panel revealed that the 5 common non-synonymous SNPs (T655C, A709G, A745G, A950T and C964A) are in significant LD with the C-154T promoter polymorphism (Table 6). For the silent polymorphisms, those in exon 3 (C97T, C219T and G237A) were generally not in LD with the remaining polymorphisms.

Frequencies of Non-Synonymous SNPs in Population Samples

The frequencies of the 5 common non-synonymous SNPs (T655C, A709G, A745G, A950T and G964A encoding S199P, K217E, T229A, Q297L, and H302N respectively) were determined in samples from individuals of different ethnic background to determine the extent of variation in the GP6 protein. These samples included a larger panel of Caucasians (n=1127), Koreans (n=63), South African blacks (n=40), Ethiopians (n=36) and Curaco (n=40). All sites tested were polymorphic in each population and significant differences in genotype frequency were observed between the populations tested (Table 7). Deviation from the Hardy-Weinberg equilibrium was observed in the Korean sample for the A709G and A745G polymorphisms, in both cases there was a deficiency of heterozygotes.

GP6 Protein Variants

The population genotyping data was used to infer the GP6 haplotypes that encoded different protein variants. This analysis identified 12 different GP6 haplotypes (Table 8). Identical results were obtained when the data was either analysed as a complete data set or as individual populations. The analysis revealed the presence of both shared and population specific GP6 haplotypes and that, in general, more haplotypes were observed in individuals of African origin.

Discussion

Glycoprotein VI (GP6) is found exclusively on platelets and brings about their activation following binding to collagen, thus playing a central role in platelet activation following exposure of the subendothelial matrix. The signaling cascade that is induced following ligation of GP6 by collagen has been studied in detail using the GP6 specific ligand CRP. Two GP6 alleles were identified following a study of 21 individuals. These alleles differ at 9 dimorphisms which encode for 5 amino acid substitutions in the mature form of the GP6 protein (Table 4). Using the dimorphisms encoding a Serine to Proline substitution at position 199 in the mature form of GP6 as a marker, Croft et al have shown an association between GP6 haplotype and the risk of myocardial infarction in a restricted patient group. We have demonstrated a functional difference between platelets from individuals who are homozygous for the 'a' and 'b' GP6 alleles. Using the GP6 specific ligand CRP we observed a significant reduction in the response to CRP in individuals homozygous for the GP6 'b' allele relative to those homozygous for the 'a' allele. This difference in reactivity prompted us to generate a high-resolution map of genetic variation at the GP6 locus. Exon re-sequencing of 188 chromosomes revealed 18 dimorphisms, 6 of which encoded amino acid substitutions in GP6 (Table 4). Taqman genotyping for 9 of these dimorphisms showed complete concordance with sequencing data. No significant differences in individual allele frequencies were observed between the core sequencing panel and a larger panel containing samples from 1 127 donors (Table 4).

Interestingly, whilst the distribution of SNPs was fairly even throughout the GP6 exons (FIG. 12), the substitution encoding mutations were largely restricted to the stem and cytoplasmic tail. Of the eight SNPs identified in the 2 Ig-like domains of GP6, only 1 encoded for an amino acid substitution, whereas, 3 of 3 SNPs in the stem and 2 of 3 SNPs in the cytoplasmic tail encoded amino acid substitutions (FIG. 12 and Table 4). The single, substitution encoding SNP identified in the 2 Ig-like, ligand-binding domains of GP6, C6080G, encoded for a conservative Leu to Val substitution at position 83 in GP6. These observations suggest that the amino acid sequence of the ligand binding domains of the GP6 have been conserved, whereas a greater level of amino acid variation has developed in the stem and cytoplasmic domains. It is possible that amino acid replacements in the 2 Ig-like domains of GP6 lead to an unacceptable reduction in collagen binding, however, work in our laboratory suggests that some point mutations have relatively little effect on the affinity of GP6 monomers for CRP and for collagen. Alternatively, the 2 Ig-like domains of GP6 may be involved in an oligomerisation process upon ligand binding and small changes in structure may affect oligomerisation leading to life-threatening pro-thrombotic or bleeding events. Genotyping for polymorphisms that have been reported to affect the expression levels of GPIbα and α2 integrin, 2 receptors involved in platelet adhesion to collagen, showed no significant association with the GP6 haplotype (Data not shown).

The 18 SNPs segregated into 37 haplotypes and significant LD was observed between all the non-synonymous SNPs and the previously described promoter polymorphism at position —154. We next genotyped the 5 common non-synonymous SNPs in a panel of samples from different ethnic backgrounds. The 5 sites were polymorphic in all populations studied with the allele frequencies differing significantly between populations (Table 7).

The genotyping data was used to determine GP6 protein haplotypes, each of which would encode a unique form of GP6 with potentially unique signalling responses. A total of 12 GP6 protein haplotypes were identified (Table 8), 8 of which were shared between populations and 4 were population specific. The haplotypes were numbered according to their prevalence in the study group. Interestingly, a third common GP6 haplotype was observed in all populations studied with a frequency between 0.13 and 0.02.

In the panel of Caucasians, 6.9% of individuals had GP6 genotypes that could not be predicted from typing at a single SNP position. This observation is of importance for genotyping studies that have been performed to determine whether GP6 is a risk factor for cardiovascular disease. In Caucasians, we observed that genotyping at 2 SNP positions (T655C and A950T) identified individuals with variant GP6 types in 99.9% of cases. For non-Caucasian populations, genotyping for more than two SNPs is required to identify variant GP6 types with the same degree of certainty. Previously, the T655C polymorphism has been shown to be a risk factor for myocardial infarction in a restricted patient group. However, by genotyping for additional SNPs in the GP6 gene we have shown that the T655C genotype does not agree with the complete GP6 genotype in 6.9% of Caucasians, information that guards against the use of a single SNP for determining GP6 genotypes.

Our study has clearly identified that the GP6 locus is highly polymorphic with 37 haplotypes. The SNPs in GP6 encode for 6 amino acid substitutions that are present in all populations studied with significantly different frequencies between populations. The 6 SNPs encode for 12 GP6 protein variants, the most common of which differ in their response to GP6 specific ligands. It is currently not known whether or not single or multiple amino acid substitutions contribute to this difference. The panel of GP6 variants that we have identified will be invaluable in elucidating the molecular mechanism of allele specific GP6 signalling.

TABLE 2

Amplication and sequencing primers

| Target exons | Primer Name | Primer Sequence (SEQ ID NO:) |
|---|---|---|
| Exon 1 | | 5'-CAGGGAGTTTATGGGAGCAC-3' (39) |
| | | 5'-CCAGCCATGAATACACTGGAA-3' (40) |
| Exon 2 + 3 | GP6for1 | 5'-AATGTCCATAAAAGCGAGTCC-3' (41) |
| | GP6rev1 | 5'-CCGTATTTGTGTCCTGAACG-3' (42) |

TABLE 2-continued

Amplication and sequencing primers

| Target exons | Primer Name | Primer Sequence (SEQ ID NO:) |
|---|---|---|
| Exon 4 | GP6for2 | 5'-AAAAAGCTCCCCAGCTCTTAG-3' (43) |
| | GP6rev2 | 5'-ATGGCCATCAGGACCTATAAA-3' (44) |
| Exon 5 | GP6for3 | 5'-TATTTGTTCAGGACCCACAGC-3' (45) |
| | GP6rev3 | 5'-AAGGGGTCCGTGTACCTCATA-3' (46) |
| Exon 6 | GP6for4 | 5'-CTCAAAAGGGGAATGGAGATA-3' (47) |
| | GP6rev4 | 5'-AAGAGAGAGCTCCGTCCTCAC-3' (48) |
| Exon 7 + 8 | GP6for5 | 5'-GGAGTAGGCACAGTGACAGG-3' (49) |
| | GP6rev5 | 5'-GTTTCCACAGCTGTAGCCTCT-3' (50) |
| | GP6rev6 | 5'-GAGTTGGCTTTGGTGAAGAGA-3' (51) |
| | GP6for7 | 5'-CTGGAGGTGGGCTCTTTC-3' (52) |

TABLE 3

Primers and probes for allelic discrimination assay

| SNP | Primers (SEQ ID NO:) | Probes (SEQ ID NO:) | Label | Tm (°C.) | Type |
|---|---|---|---|---|---|
| C307G | 5'-GACGCTACCGCTGCTCCTAC-3' (53) | 5'-CGACCAGCTGGAG-3' (69) | Fam | 55 | MGB |
| | 5'-TCCGATCCCCCTTCCTTTAC-3' (54) | 5'-CGACCAGGTGGAGC-3' (70) | Vic | | |
| C484A | 5'-GGGACCCTGCGCCCTAC-3' (55) | 5'-TAGCCCTGTACCATCTC-3' (71) | Fam | 60 | MGB |
| | 5'-GGCGGTCACCGTGATGAT-3' (56) | 5'-TAGCCCGGTACCATCT-3' (72) | Vic | | |
| T655C | 5'-TCCCAGGAACCTCTGTGACC-3' (57) | 5'-AGAACCACCTTCCTCGGTAGCAGGTAG-3' (73) | Fam | 60 | STD |
| | 5'-CTCATACGCTGTGCACCAGAA-3' (58) | 5'-ACCACCTTCCCCGGTAGCAGGT-3' (74) | Vic | | |
| A709G | 5'-CTCAGAAGCCACCGCTGAA-3' (59) | 5'-TCACAAACAAAGTCTT-3' (75) | Fam | 55 | MGB |
| | 5'-CTGAGCATGAAATGCCTGGTT-3' (60) | 5'-CACAAACGAAGTCT-3' (76) | Vic | | |
| A745G | 5'-TTTCACACTTAGCCTTTGTTTGGTT-3' (61) | 5'-TTCTAGGAGTATCACCACCAGT-3' (77) | Fam | 60 | MGB |
| | 5'-CCAGCTGGAGAGTCTGACTCCTT-3' (62) | 5'-CTAGGAGTATCACCGCCAGT-3' (78) | Vic | | |
| G936C | 5'-TGGCACAGCCGGAGGAA-3' (63) | 5'-TTCCGCCCCTGCCG-3' (79) | Fam | 55 | MGB |
| | 5'-ACATCCTGTCGGCCTCCAT-3' (64) | 5'-TTCCGCCCCTCCCG-3' (80) | Vic | | |
| A950T | 5'-AAGCGCCTGCGGCAC-3' (65) | 5'-CCTCCCGCAGACCCGGAAA-3' (81) | Fam | 60 | STD |
| | 5'-ACATAACCCGCGGCTGTG-3' (66) | 5'-CCTCCCGCTGACCCGGAAA-3' (82) | Vic | | |
| C964A | 5'-AGGAAGCGCCTGCGG-3' (67) | 5'-CTGACCCCGTGTGATTTCCG-3' (83) | Fam | 60 | STD |
| | 5'-TCCCATGCCATGATCCCT-3' (68) | 5'-TCCTGACCCCGTTTGATTTCC-3' (84) | Vic | | |

TABLE 4

Frequencies of SNPs identified in GP6

| Mature GP6 codon | cDNA | Genomic nucleotide | Croft et al | dbSNP ID | Nucleotide Variation | Protein residue | Sequencing panel frequency | Panel 1 frequency |
|---|---|---|---|---|---|---|---|---|
| | −222 | | | | G | NA | 0.995 | nt |
| | | | | | A | | 0.005 | |
| | −154 | | | | C | NA | 0.489 | |
| | | | | | T | | 0.511 | |
| | −143 | | | | C | NA | 0.995 | nt |
| | | | | | T | | 0.005 | |
| | 15 | | | | G | Pro | 0.995 | nt |
| | | | | | A | Pro | 0.005 | |
| 13 | 97 | | 5870 | | C | Leu | 0.979 | nt |
| | | | | | T | Leu | 0.021 | |
| 53 | 219 | | 5992 | | C | Leu | 0.936 | nt |
| | | | | | T | Leu | 0.064 | |

TABLE 4-continued

Frequencies of SNPs identified in GP6

| Mature GP6 codon | cDNA | Genomic nucleotide | Croft et al | dbSNP ID | Nucleotide Variation | Protein residue | Sequencing panel frequency | Panel 1 frequency |
|---|---|---|---|---|---|---|---|---|
| 59 | 237 | 6010 | | | G | Lys | 0.904 | nt |
| | | | | | A | Lys | 0.096 | |
| 83 | 307 | 6080 | | | C | Leu | 0.995 | 0.995 |
| | | | | | G | Val | 0.005 | 0.005 |
| 142 | 484 | 10533 | 10781 | rs892090 | C | Arg | 0.819 | 0.840 |
| | | | | | A | Arg | 0.181 | 0.160 |
| 145 | 495 | 10544 | | rs892089 | C | Phe | 0.793 | nt |
| | | | | | T | Phe | 0.207 | |
| 149 | 507 | 10556 | 10804 | | G | Thr | 0.767 | nt |
| | | | | | A | Thr | 0.233 | |
| 172 | 576 | 10625 | 10873 | rs1654425 | G | Ser | 0.824 | nt |
| | | | | | A | Ser | 0.176 | |
| 199 | 655 | 13010 | 13254 | rs1613662 | T | Ser | 0.814 | 0.842 |
| | | | | | C | Pro | 0.186 | 0.158 |
| 217 | 709 | 19570 | 19871 | rs1654416 | A | Lys | 0.809 | 0.825 |
| | | | | | G | Glu | 0.191 | 0.175 |
| 229 | 745 | 22524 | 21908 | rs2304167 | A | Thr | 0.798 | 0.821 |
| | | | | | G | Ala | 0.202 | 0.179 |
| 292 | 936 | 23232 | 22616 | | G | Leu | 0.697 | 0.654 |
| | | | | | C | Leu | 0.303 | 0.346 |
| 297 | 950 | 23246 | 22630 | | A | Gln | 0.793 | 0.820 |
| | | | | | T | Leu | 0.207 | 0.180 |
| 302 | 964 | 23260 | 22644 | | C | His | 0.814 | 0.843 |
| | | | | | A | Asn | 0.186 | 0.157 |

Where possible, the dbSNP reference ID is given.
nt = not tested

TABLE 5

Sequence haplotypes observed in GP6

| Sequence Haplotype No. | -2 2 G | -1 5 C | -1 4 C | 2 1 G | 2 9 C | 3 7 C | 4 4 G | 4 5 C | 5 7 C | 5 6 C | 6 5 G | 7 9 G | 7 5 T | 7 6 A | 9 0 A | 9 4 G | 9 6 A C | Observed |
|---|---|---|---|---|---|---|---|---|---|---|---|---|---|---|---|---|---|---|
| H3 | . | . | . | . . . . . . . . . . . . . . . | 27 |
| H8 | . | . | . | . . . . . . . . . . . . . C . . | 7 |
| H15 | . | . | . | . . . . . . . . G G C T A . . | 1 |
| H16 | . | . | . | . . . . . . . . C G G C T A . . | 1 |
| H17 | . | . | . | . . . . . A . . . . . . . . . | 1 |
| H18 | . | . | . | . . . . T . . . . . . . . . . | 1 |
| H19 | . | . | . | . . . . T . . . . G C T . . . | 1 |
| H20 | . | . | . | . . . A T . A . . . . . . . . | 1 |
| H6 | . | . | . | . . . A T . A C G G . . . . . | 9 |
| H5 | . | . | . | . . . A T . A C G G C T A . . | 13 |
| H21 | . | . | . | . . . . G . . . . . . . . . . | 1 |
| H7 | . | . | . | . . . A . . . . . . . . . . . | 8 |
| H22 | . | . | . | . . . A . . . . . . . . . C . . | 1 |
| H10 | . | . | . | . . . A . . . . . C G G . T A . | 2 |
| H11 | . | . | . | . . . A . A T . A C . . . C . . | 2 |
| H23 | . | . | . | . . . A . A T . A C G G C T A . | 1 |
| H9 | . | . | . | . . . . T . . . . . . . . . . | 6 |
| H24 | . | . | . | . . . . T . . . . . . . . C . . | 1 |
| H12 | . | . | . | . . . . T . . A T . A C G G C T A | 2 |
| H13 | . | . | . | . . . . T A . . . . . . . . . | 2 |
| H25 | . | . | . | . . . T . . . . . . . . . . . | 1 |
| H26 | . | . | . | . . . . T . . A . . A C G G C . . | 1 |
| H2 | . | T | . | . . . . . . . . . . . . . . . | 30 |
| H4 | . | T | . | . . . . . . . . . . . . . C . . | 16 |
| H27 | . | T | . | . . . . . . . . . C G G . T A . | 1 |
| H1 | . | T | . | . . . . . . . . A . . . . . . | 37 |
| H28 | . | T | . | . . . . . . T . . . G G . T . . | 1 |
| H14 | . | T | . | . . . . . . T . . . G G C T . . | 2 |
| H29 | . | T | . | . . . . . A T . A C G G . T A . | 1 |
| H30 | . | T | . | . . T A . . . . . . . . . . . | 1 |
| H31 | . | T | . | . T . . . A T . . . . . C T A . | 1 |

TABLE 5-continued

Sequence haplotypes observed in GP6

| Sequence Haplotype No. | -2 2 G | -1 5 4 C | -1 4 3 C | 1 9 5 G | 2 3 7 C | 2 0 9 C | 3 8 7 G | 4 9 4 C | 4 5 5 C | 5 7 6 G | 6 5 5 G | 7 9 5 T | 7 0 6 A | 5 9 0 A | 9 5 4 G | 9 6 0 A | 9 4 C | Ob-served |
|---|---|---|---|---|---|---|---|---|---|---|---|---|---|---|---|---|---|---|
| H32 | . | T | . | . | T | . | A | . | . | . | A | . | . | . | . | . | . | 1 |
| H33 | . | T | . | A | . | . | . | . | . | . | . | . | . | . | . | . | . | 1 |
| H34 | . | T | C | . | . | . | . | . | . | . | A | . | . | . | . | . | . | 1 |
| H35 | A | T | . | . | T | . | . | . | . | . | . | . | . | . | C | . | . | 1 |
| H36 | ? | ? | ? | ? | . | . | . | . | . | . | A | A | . | G | . | . | T | . | 1 |
| H37 | ? | ? | ? | ? | . | . | . | . | A | T | . | . | C | . | G | . | . | A | 1 |

'?' denotes missing data, non-synonymous SNPs are shaded in grey

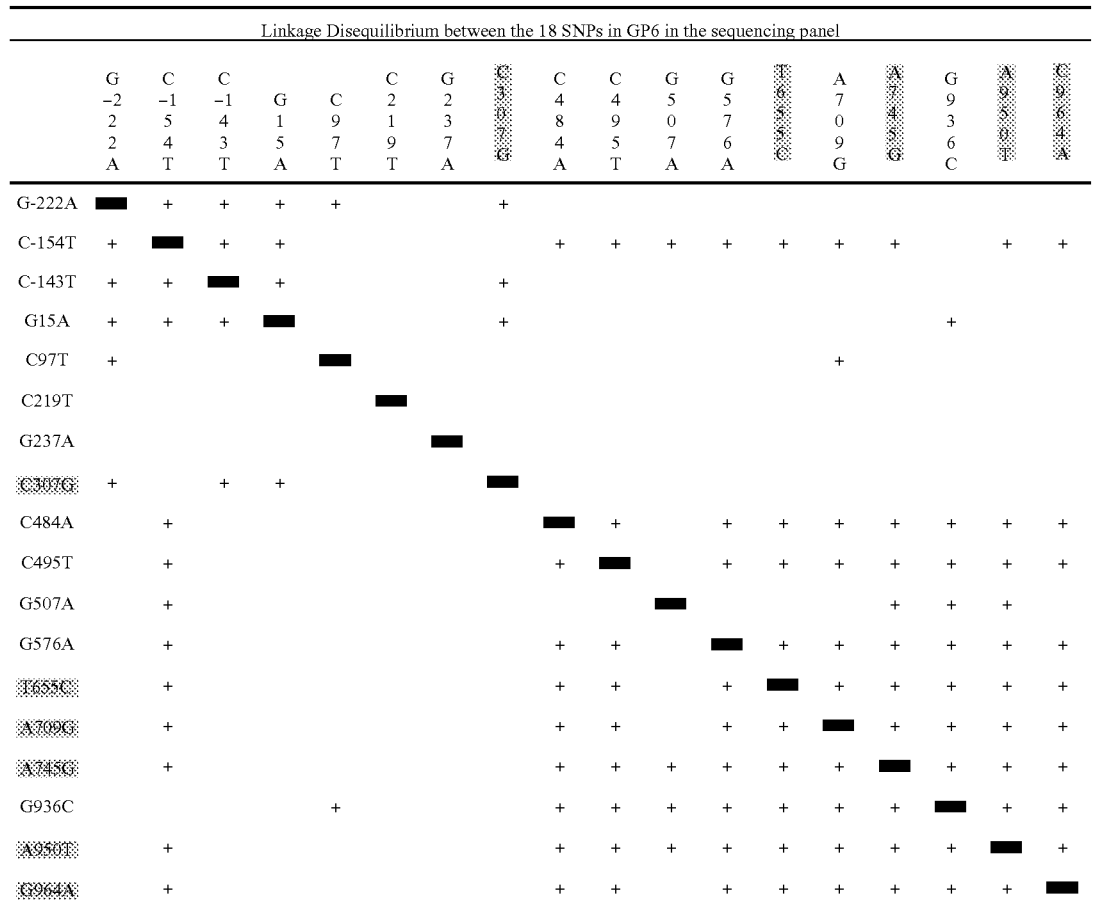

TABLE 6

Linkage Disequilibrium between the 18 SNPs in GP6 in the sequencing panel

'+' denotes LD (p < 0.04, Fishers Exact Test), non-synonymous SNPs are shaded in grey

TABLE 7

Frequency of GP6 "b" allele in population study.
Figures if brackets relate to the number of individuals tested for each genotype

| Nucleotide<br>Amino acid | T655C<br>S199P | A709G<br>K217E | A745G<br>T229A | A950T<br>Q297L | G964A<br>H302N |
|---|---|---|---|---|---|
| Koreans (63) | 0.024 | 0.169 (62) | 0.185 (62) | 0.183 | 0.041 (49) |
| SA Blacks (40) | 0.325 | 0.475 | 0.613 | 0.551 (39) | 0.474 (39) |

TABLE 7-continued

Frequency of GP6 "b" allele in population study.
Figures if brackets relate to the number of individuals tested for each genotype

| Nucleotide | T655C | A709G | A745G | A950T | G964A |
|---|---|---|---|---|---|
| Amino acid | S199P | K217E | T229A | Q297L | H302N |
| Curaco (40) | 0.288 | 0.423 (39) | 0.488 | 0.462 (39) | 0.363 |
| Ethiopians (36) | 0.242 (31) | 0.290 (31) | 0.403 | 0.310 (29) | 0.368 (34) |
| Panel 1 (1127) | 0.159 | 0.165 | 0.167 | 0.167 | 0.160 |
| Sequencing panel (94) | 0.186 | 0.197 | 0.202 | 0.202 | 0.181 |

TABLE 8

GP6 protein variants

| GP6 Protein No. | 655T | 709A | 745A | 950A | 964C | 199 | 217 | 229 | 297 | 302 | P1 | Kor | SAB | Eth | Cur |
|---|---|---|---|---|---|---|---|---|---|---|---|---|---|---|---|
| a | . | . | . | . | . | S | K | T | Q | H | 1833 | 87 | 28 | 36 | 41 |
| b | C | G | G | T | A | P | E | A | L | N | 342 | 2 | 26 | 13 | 21 |
| c | . | G | G | T | . | S | E | A | L | H | 51 | 6 | 10 | 1 | 7 |
| d | . | . | G | T | A | S | K | A | L | N | 8 | | 7 | 1 | 3 |
| e | C | . | . | . | . | P | K | T | Q | H | 15 | | | 1 | |
| f | . | G | G | T | A | S | E | A | L | N | 2 | | | 2 | 5 |
| g | . | . | G | . | . | S | K | A | Q | H | 1 | | 1 | | 1 |
| h | . | . | G | . | A | S | K | A | Q | N | | | 2 | 1 | |
| i | . | . | . | T | A | S | K | T | L | N | 2 | | | | |
| j | . | G | G | . | A | S | E | A | Q | N | | | 2 | | |
| k | C | . | G | . | A | P | K | A | Q | N | | | | 1 | |
| l | C | G | G | . | A | P | E | A | Q | N | 1 | | | | |

EXAMPLE 3

Introduction

Damage to blood vessels exposes circulating platelets to the extracellular matrix. Here, collagen supports adhesion and stimulates platelet activation by acting as a ligand for a number of platelet receptors. Platelets are first tethered by the interaction of glycoprotein (GP) Ibα with the A1 domain of von Willebrand Factor (vWF), a plasma protein that binds to exposed collagen. Firm platelet adhesion results from the concerted action of the collagen receptor GPIaIIa (integrin α2β1) and the fibrinogen receptor GPIIbIIIa (αIIbβ3) which also binds immobilised vWF. Collagen mediated activation of platelets is dependent upon the engagement and clustering of GPVI, an immunoglobulin (Ig) superfamily member with homology to killer-cell Ig-like receptors (KIRs) and the FcαRI. We and others have recently described the ligand binding sites of α2 integrin and GPIbα at the structural level.

Glycoprotein (GP) VI is the major receptor responsible for platelet activation by collagen, but the collagen-binding surface of GPVI is unknown. Recent work has demonstrated the key role played by GPVI in arterial thrombus formation in mice and provides a clear basis for the development of potentially therapeutic GPVI inhibitors. Indeed, blockade of GPVI is attractive for several reasons. Firstly, the expression of GPVI is restricted to platelets and megakaryocytes. Secondly, collagen is required for prothrombotic 'COAT' platelet formation, for which blockade of GPVI may provide a specific control point. Thirdly, patients with congenital or acquired autoantibody-mediated GPVI deficiency have only a mild bleeding disorder, despite having a significantly reduced platelet response to collagen. These observations have been recently confirmed in mice.

The GPVI gene is part of the human leukocyte receptor cluster (LRC) on chromosome 19q13.4[15]. GPVI has two extracellular C2-type Ig-like domains (D1 and D2). These Ig-like domains are connected by a glycosylated stem of ~60 amino acids to a transmembrane sequence within which an arginine residue forms a salt-bridge with a transmembrane aspartate in the FcR γ chain. GPVI signalling is dependent upon its' interaction with the γ chain. The 51 residue cytoplasmic domain of human GPVI has binding sites for various signalling proteins. Two modes of ligand binding for LRC members have been described. The KIRs bind to HLA via a surface that contains the interdomain linker, whereas FcαRI binds IgA via its' N-terminal Ig-like domain. Previous studies have shown that GPVI recognises glycine-proline-hydroxyproline (GPO) repeat motifs in the triple helical structure of collagen. It was also shown that collagen related peptide (CRP), which contains 10 GPO motifs and spontaneously forms helices under physiological conditions is a powerful and specific agonist for GPVI. GPVI specifically recognises CRP but not a peptide of similar structure (GPP10) lacking hydroxyproline. Studies with GPVI-deficient murine platelets and the inhibitory monoclonal antibody JAQ-1 are suggestive of the existence of two collagen binding sites on GPVI, the primary one being the binding site for CRP.

Here, we describe experiments which reveal the primary collagen-binding site to a particular surface of GPVI using the aforementioned peptides. By homology modelling of the Ig-like domains of human and murine GPVI on basis of the KIR coordinates, residues of possible relevance to CRP binding were identified. On that basis, twelve D1D2 molecules (wild type human and mouse and ten mutants of human) were recombinantly expressed and their relative binding affinities for CRP determined. The wild type hD1D2 was used as a bait to select inhibitory (clone 10B12) and non-inhibitory phage antibodies (clone 1C3) specific for GPVI. Results of epitope mapping of the former and the modelling of interface of antibody 10B12 and GPVI combined with the results obtained with the mutant D1D2 molecules allowed the identification of the primary collagen-binding surface on GPVI.

Selection of Phage Antibodies binding to hD1D2

Human single chain variable domain antibody fragments (scFv) can be selected from repertoires of human antibodies displayed on the surface of philamentous phage. Antibodies specific for antigen can be obtained from such libraries by rounds of phage affinity selection followed by expansion of selected and antigen specific phage. Once antigen-specific 'phage antibodies' have been obtained the genes encoding the Variable domains of Heavy (VH) and Light (VL) chains of the antibody can be rescued. Using such an approach we selected from two human V gene phage display libraries, Marks (Marks et al, Biotechnology NY, 1993; 11; 1145-9) and CAT (Vaughan et al, Nat. Biotechnol. 1996; 14:309-14), scFvs specific for GPVI. For both libraries, an identical protocol was used for the first round of selection. Briefly, phage were mixed with bD1D2 in solution and complexes were then captured via the CaM tag onto the surface of BSA-N9A coated immunotubes. After extensive washing, the phage antibody-bD1D2 complexes were eluted by chelating calcium with 10 mM EDTA and then propagated in $E.$ $coli$ as previously described (Watkins et al, Tissue Antigens, 2000; 55:219-28). For the Marks library, this protocol was repeated twice and clones from the third round of selection screened for binding to hD1D2 by ELISA. For the CAT library, the second round of selection was designed to enrich for scFvs that specifically blocked the CRP-DlD2 interaction. In detail, pre-formed, immobilised hD1D2-CRP complexes were obtained by incubating CaM tagged D1D2 in wells coated with CRP. Regrown phage particles from the first round were added to these wells and allowed to compete with CRP for binding to hD1D2, thus releasing phage-hD1D2 complexes into solution. These complexes were captured via the CaM tag, washed and eluted with EDTA as before. Clones from this second round of selection were extensively screened for specificity.

In this manner two clones 10B12 and 1C3 were selected and the antibodies thus obtained characterised.

The VH and VL genes of both clones were sequenced as previously described (Watkins et al, Tissue Antigens, 2000; 55:219-28) and nucleotide sequences compared with germline V-gene sequences in the V-base directory (Cook et al, Immunology Today, 1995; 16:237-42). The scFv gene cassettes of both clones were subcloned into the pUCl 19-Sfi/Not-His6 vector and scFv expressed as described previously described (Watkins et al, Tissue Antigens, 2000; 55:219-28) and purified as above. The specificity of selected scFvs 10B12 and 1C3 was investigated:

- by ELISA with a panel of proteins either captured via the CaM tag to BSA-N9A coated plates in the presence of $Ca^{2+}$, or coated directly onto the microplate wells.
- by measuring the binding of the scFvs to blood cells by flow cytometry with positive binding to platelets and no binding to other blood cells
- By showing the ability of soluble recombinant GPVI (residues 1-186) to inhibit the binding of both scFvs to platelets In platelet aggregometry, it was observed that scFv 10B12 but not scFv 1C3 was able to inhibit the aggregation of platelets induced by either collagen type I fibres (Ethicon, Somerville, N.J., USA) or collagen related peptide. The inhibitory antibody 10B12 did not abrogate platelet aggregation induced by other platelet agonists which do activate platelets via alternative signalling pathways then GPVI, such as adenosine 5'-diphosphate (ADP; Sigma), U46619 (Sigma), thrombin receptor activating peptide (TRAP; Sigma) or epinephrine (EPI; Sigma). ScFv 10B12 was also able to inhibit the formation of thrombi in flowing whole blood over a surface coated with collagen. Perfusion flow assays were performed as previously described (Roest et al, Blood, 2000; 96: 1433-7). In sharp contrast scFv 1C3 had no ability to inhibit the aggregation of platelets induced by collagen or CRP or reduce the thrombus formation in whole blood.

Measurement of real-time interactions between recombinant GPVI proteins and the two scFvs was used to show that the two antibodies 10B12 and 1C3 (inhibitor and non-inhibitor) were against different epitopes on GPVI. Studies with 12 GPVI recombinant proteins (residue 1-186, human and murine forms and 10 human mutants) were used to obtain information on the epitope recognised by the inhibitory antibody 10B12. Surprisingly only one mutant Lysine59Glutamate showed reduced reactivity with scFv10B12. The same mutant showed a grossly reduced reactivity with CRP.

Modelling of the 10B12-GPVI interface using information on wild type human GPVI and the K59E mutant provided insight into the epitope recognised by scFv 10B12. The highly acidic H3 loop of the VH domain of 10B12 forms part of a negatively charged region in the antigen-binding surface of the antibody. This surface has both charge and shape complementarity with a basic multi-lobed patch on the apical surface of human GPVI. The modelling supports the notion that this lobed patch is at the centre of the 10B 12 epitope. The basic patch on human GPVI appears to be formed by residues R38, K41, R46, K59 and R60. The K59E mutation reduces the basic nature of the patch whilst the surrounding features are preserved explaining the reduced binding of 10B12 to the K59E mutant of human GPVI. The model generated is compatible with a footprint of the antibody which would cover the interdomain linker and extend to the apical surface of the second domain.

The availability of two recombinant antibodies against different but non polymorphic epitopes on GPVI allows the development of simple immunoassays for the measurement of human GPVI levels. This can be applied to determine i.e. the overall level of GPVI in platelets, the amount of GPVI displayed on the platelet membrane and the levels of soluble GPVI in plasma. Such measurements provide an alternative method to determine the GPVI alleles present in a certain individual as the amount of GPVI is linked to the haplotype of the GPVI gene. Measuring GPVI levels may be of relevance to determine the extent of platelet activation in certain clinical conditions (i.e. arterial thrombus formation, thrombocytopenic thrombotic purpura, heparin induced thrombocytopenia and thrombosis, disseminated intravascular coagulation). Alternatively measurement of GPVI levels may be used to determine the appropriate levels of a GPVI inhibitory drug to be administered, or may lead to the adjustment of the dosing of other anti-thrombotics.

To conclude, using site-directed mutagenesis of the GPVI protein and human antibodies against GPVI converging evidence has been obtained to localise the collagen related peptide/primary collagen binding surface of GPVI to the area where the first domain meets the interdomain linker.

Human antibodies against human GPVI, including 10B12 and 1C3, are also the subject of International patent application No. PCT/GB01/005755.

The invention claimed is:

1. A method of diagnosing whether a subject has an increased risk of bleeding, comprising a step of detecting that is selected from:
   (A) detecting presence or absence of at least two single nucleotide polymorphisms (SNPs) in a nucleic acid of a sample obtained from a Caucasian subject to determine whether the subject is homozygous for a GPVI$^b$ allele, wherein presence of the GPVI$^b$ allele is indicated by a GPVI allele with a C nucleotide at position 655 of SEQ ID NO:1, or at a corresponding position encoding amino acid position 199 of mature GPVI amino acid sequence, or dbSNP ID rs1613662, and a T nucleotide at position 950 of SEQ ID NO:1, or at a corresponding position encoding amino acid position 297 of mature GPVI amino acid sequence, wherein homozygosity for the GPVI$^b$ allele indicates that the Caucasian has an increased risk of bleeding compared to a Caucasian lacking the GPVI$^b$ allele, and
   (B) detecting presence or absence of at least five single nucleotide polymorphisms (SNPs) in a nucleic acid of a sample obtained from a non-Caucasian subject to determine whether the subject is homozygous for a GPVI$^b$ allele, wherein presence of the GPVI$^b$ allele is indicated by a GPVI allele with a C nucleotide at position 655 of SEQ ID NO:1, or at a corresponding position encoding amino acid position 199 of mature GPVI amino acid sequence, or dbSNP ID rs1613662, a G nucleotide at position 709 of SEQ ID NO:1, or at a corresponding position encoding amino acid position 217 of mature GPVI amino acid sequence, or dbSNP ID rs1654416, a G nucleotide at position 745 of SEQ ID NO:1, or at a corresponding position encoding amino acid position 229 of mature GPVI amino acid sequence, or dbSNP ID rs2304167, a T nucleotide at position 950 of SEQ ID NO:1, or at a corresponding position encoding amino acid position 297 of mature GPVI amino acid sequence, and an A nucleotide at position 964 of SEQ ID NO:1, or at a corresponding position encoding amino acid position 302 of mature GPVI amino acid sequence, wherein homozygosity for the GPVI$^b$ allele indicates that the non-Caucasian has an increased risk of bleeding compared to a non-Caucasian lacking the GPVI$^b$ allele; and
   diagnosing that the subject has an increased risk of bleeding if the subject is homozygous for the GPVI$^b$ allele.

2. The method according to claim 1 which comprises a step of amplifying nucleic acid obtained or derived from the subject.

3. The method according to claim 1 which comprises detecting the SNPs by a method that comprises a method that is selected from the group consisting of real-time PCR and fluorimetric analysis.

4. The method according to claim 1 wherein detecting comprises restriction enzyme analysis.

5. A method for diagnosing an increased risk of bleeding, comprising a step of assaying that is selected from:
   (A) assaying binding of one or more probes to nucleic acid of, or derived from, a sample obtained from a Caucasian subject to determine whether the subject is homozygous for a GPVI$^b$ allele, wherein the one or more probes bind specifically to a region of GPVI nucleic acid that comprises at least two SNPs distinctive of a GPVI allele, wherein presence of the GPVI$^b$ allele is indicated by a GPVI allele with a C nucleotide at position 655 of SEQ ID NO:1, or at a corresponding position encoding amino acid position 199 of mature GPVI amino acid sequence, or dbSNP ID rs1613662, and a T nucleotide at position 950 of SEQ ID NO: 1, or at a corresponding position encoding amino acid position 297 of mature GPVI amino acid sequence, and wherein homozygosity for the GPVI$^b$ allele indicates that the Caucasian has an increased risk of bleeding compared to a Caucasian lacking the GPVI$^b$ allele, and
   (B) assaying binding of one or more probes to nucleic acid of, or derived from, a sample obtained from a non-Caucasian subject to determine whether the subject is homozygous for a GPVI$^b$ allele, wherein the one or more probes bind specifically to a region of GPVI nucleic acid that comprises at least five SNPs distinctive of a GPVI allele, and presence of the GPVI$^b$ allele is indicated by a GPVI allele with a C nucleotide at position 655 of SEQ ID NO: 1, or at a corresponding position encoding amino acid position 199 of mature GPVI amino acid sequence, or dbSNP ID rs1613662, a G nucleotide at position 709 of SEQ ID NO: 1, or at a corresponding position encoding amino acid position 217 of mature GPVI amino acid sequence, or dbSNP ID rs1654416, a G nucleotide at position 745 of SEQ ID NO: 1, or at a corresponding position encoding amino acid position 229 of mature GPVI amino acid sequence, or dbSNP ID rs2304167, a T nucleotide at position 950 of SEQ ID NO: 1, or at a corresponding position encoding amino acid position 297 of mature GPVI amino acid sequence, and an A nucleotide at position 964 of SEQ ID NO: 1, or at a corresponding position encoding amino acid position 302 of mature GPVI amino acid sequence, and wherein homozygosity for the GPVI$^b$ allele indicates that the non-Caucasian has an increased risk of bleeding compared to a non-Caucasian lacking the GPVI$^b$ allele; and
   diagnosing that the subject has an increased risk of bleeding if the subject is homozygous for the GPVI$^b$ allele.

6. A method for diagnosing an increased risk of bleeding, comprising a step of amplifying that is selected from:
   (A) amplifying nucleic acid of, or derived from, a sample obtained from a Caucasian subject to determine whether the subject is homozygous for a GPVI$^b$ allele, wherein amplification is carried out with one or more primers that amplify a GPVI nucleic acid which includes at least two SNPs distinctive of a GPVI allele, wherein presence of the GPVI$^b$ allele is indicated by a GPVI allele with a C nucleotide at position 655 of SEQ ID NO: 1, or at a corresponding position encoding amino acid position 199 of mature GPVI amino acid sequence, or dbSNP ID rs1613662, and a T nucleotide at position 950 of SEQ ID NO: 1, or at a corresponding position encoding amino acid position 297 of mature GPVI amino acid sequence, and wherein homozygosity for the GPVI$^b$ allele indicates that the Caucasian has an increased risk of bleeding compared to a Caucasian lacking the GPVI$^b$ allele, and (B) amplifying nucleic acid of, or derived from, a sample obtained from a non-Caucasian subject to determine whether the subject is homozygous for a GPVI$^b$ allele, wherein amplification is carried out with one or more primers that amplify a GPVI nucleic acid which includes at least five SNPs distinctive of a GPVI allele, wherein presence of the GPVI$^b$ allele is indicated by a GPVI allele with a C nucleotide at position 655 of SEQ ID NO: 1, or at a corresponding position encoding amino acid position 199 of mature GPVI amino acid sequence, or dbSNP ID rs1613662, a G nucleotide at position 709 of SEQ ID NO: 1, or at a corresponding position encoding amino acid position 217 of mature GPVI amino acid sequence, or dbSNP ID rs1654416, a G nucleotide at position 745 of SEQ ID NO: 1, or at a corresponding position encoding amino acid position 229 of mature GPVI amino acid sequence, or dbSNP ID rs2304167, a T nucleotide at position 950 of SEQ ID NO: 1, or at a corresponding position encoding amino acid position 297 of mature GPVI amino acid sequence, and an A nucleotide at position 964 of SEQ ID NO: 1, or at a corresponding position encoding amino acid position 302 of mature GPVI amino acid sequence, and wherein homozygosity for the GPVI$^b$ allele indicates that the non-Caucasian has an increased risk of bleeding compared to a non-Caucasian lacking the GPVI$^b$ allele; and diagnosing that the subject has an increased risk of bleeding if the subject is homozygous for the GPVI$^b$ allele.

7. The method according to claim 1, wherein the subject is in need of surgery.

8. The method according to claim 7, which further comprises at least one step that is selected from the group consisting of (i) administering a drug to reduce risk of bleeding during surgery, (ii) increasing dosage of a drug to reduce the risk of bleeding during surgery, and (iii) increasing availability of donor blood if the subject is determined to have a GPVI$^b$ allele.

9. The method according to claim 1, wherein the subject has a low platelet count.

10. The method of claim 9 wherein the low platelet count is due to low endogenous platelet production, or to increased destruction or consumption of platelets.

11. The method of claim 9, which further comprises administering donor platelets to the subject if the platelet count is below 20×10$^9$/L and if the subject is determined to have a GPVI$^b$ allele.

12. The method according to claim 1 wherein the subject has an inherited or an acquired bleeding disorder.

13. The method according to claim 12 wherein the inherited or acquired bleeding disorder is selected from (a) an inherited bleeding disorder that is selected from the group consisting of Haemophilia A, Haemophilia B, Von Willebrands' disease, and Glanzmann thrombasthenia; and (b) an acquired bleeding disorder that comprises a coagulopathy.

14. The method according to claim 1 wherein the subject is being administered, or is in need of, a drug that is selected from a blood thinning drug and a drug which reduces risk of thrombus formation.

15. The method according to claim 14, which further comprises reducing dosage of the blood thinning drug or the drug which reduces risk of thrombus formation if the subject is determined to have a GPVI$^b$ allele.

16. The method according to claim 14 wherein the blood thinning drug comprises an inhibitor of collagen-mediated platelet activation that is selected from the group consisting of (i) an antibody or antibody fragment that binds to a GPVI C2-like ectodomain, (ii) a drug directed to a protein that associates directly with a GPVI intracellular domain, (iii) a drug directed to a protein that associates with FcR gamma, and (iv) a drug directed to a protein that is downstream from the protein of either (ii) or (iii) in GPVI -mediated signalling.

17. The method according to claim 1 wherein the subject is a candidate blood donor.

18. The method of claim 17, which further comprises preventing the donor from donating platelets if the subject is determined to be GPVI$^b$ allele homozygous.

19. The method according to claim 1 wherein the subject is a participant in a clinical trial to assess a candidate drug that is selected from the group consisting of a blood thinning drug and a drug which reduces risk of thrombus formation.

* * * * *

SEQUENCE LISTING

<160> NUMBER OF SEQ ID NOS: 90

<210> SEQ ID NO 1
<211> LENGTH: 1089
<212> TYPE: DNA
<213> ORGANISM: Homo sapiens

<400> SEQUENCE: 1

```
atgtctccat ccccgaccgc cctcttctgt cttgggctgt gtctggggcg tgtgccagcg        60
cagagtggac cgctcccaa gccctccctc caggctctgc ccagctccct ggtgcccctg       120
gagaagccag tgaccctccg gtgccaggga cctccgggcg tggacctgta ccgcctggag       180
aagctgagtt ccagcaggta ccaggatcag gcagtcctct tcatcccggc catgaagaga       240
agtctggctg gacgctaccg ctgctcctac cagaacggaa gcctctggtc cctgcccagc       300
gaccagctgg agctcgttgc cacgggagtt tttgccaaac cctcgctctc agcccagccc       360
ggcccggcgg tgtcgtcagg aggggacgta accctacagt gtcagactcg gtatggcttt       420
gaccaatttg ctctgtacaa ggaaggggac cctgcgccct acaagaatcc cgagagatgg       480
taccgggcta gtttccccat catcacggtg accgccgccc acagcggaac ctaccgatgc       540
tacagcttct ccagcaggga cccatacctg tggtcggccc cagcgacccc ctggagctt       600
gtggtcacag gaacctctgt gacccccagc cggttaccaa cagaaccacc ttcctcggta       660
gcagaattct cagaagccac cgctgaactg accgtctcat tcacaaacaa agtcttcaca       720
actgagactt ctaggagtat caccaccagt ccaaaggagt cagactctcc agctggtcct       780
gcccgccagt actacaccaa gggcaacctg gtccggatat gcctcggggc tgtgatccta       840
ataatcctgg cggggtttct ggcagaggac tggcacagcc ggaggaagcg cctgcggcac       900
aggggcaggg ctgtgcagag gccgcttccg cccctgccgc ccctcccgca gacccggaaa       960
tcacacgggg gtcaggatgg aggccgacag gatgttcaca gccgcgggtt atgttcatga      1020
ccgctgaacc ccaggcacgg tcgtatccaa gggagggatc atggcatggg aggcgactca      1080
tgagggcac                                                             1089
```

<210> SEQ ID NO 2
<211> LENGTH: 339
<212> TYPE: PRT
<213> ORGANISM: Homo sapiens

<400> SEQUENCE: 2

```
Met Ser Pro Ser Pro Thr Ala Leu Phe Cys Leu Gly Leu Cys Leu Gly
1               5                   10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                85                  90                  95

Ser Leu Pro Ser Asp Gln Leu Glu Leu Val Ala Thr Gly Val Phe Ala
            100                 105                 110
```

```
Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
        195                 200                 205

Pro Ser Arg Leu Pro Thr Glu Pro Pro Ser Ser Val Ala Glu Phe Ser
    210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Leu Val Arg
            260                 265                 270

Ile Cys Leu Gly Ala Val Ile Leu Ile Ile Leu Ala Gly Phe Leu Ala
        275                 280                 285

Glu Asp Trp His Ser Arg Arg Lys Arg Leu Arg His Arg Gly Arg Ala
    290                 295                 300

Val Gln Arg Pro Leu Pro Pro Leu Pro Pro Leu Pro Gln Thr Arg Lys
305                 310                 315                 320

Ser His Gly Gly Gln Asp Gly Gly Arg Gln Asp Val His Ser Arg Gly
                325                 330                 335

Leu Cys Ser

<210> SEQ ID NO 3
<211> LENGTH: 1089
<212> TYPE: DNA
<213> ORGANISM: Homo sapiens

<400> SEQUENCE: 3
atgtctccat ccccgaccgc cctcttctgt cttgggctgt gtctggggcg tgtgccagcg      60
cagagtggac cgctccccaa gccctccctc caggctctgc ccagctccct ggtgcccctg     120
gagaagccag tgaccctccg gtgccaggga cctccgggcg tggacctgta ccgcctggag     180
aagctgagtt ccagcaggta ccaggatcag gcagtcctct tcatcccggc catgaagaga     240
agtctggctg gacgctaccg ctgctcctac agaacggaag cctctggtc cctgcccagc     300 gaccagctgg agctcgttgc cacgggagtt tttgccaaac cctcgctctc agcccagccc     360
ggcccggcgg tgtcgtcagg aggggacgta accctacagt gtcagactcg gtatggcttt     420
gaccaatttg ctctgtacaa ggaagggac cctgcgccct acaagaatcc gagagatgg      480 taccgggcta gtttccccat catcacggta accgccgccc acagcggaac ctaccgatgc     540
tacagcttct ccagcaggga cccatacctg tggtcggccc cagcgacccc ctggagctt      600 gtggtcacag gaacctctgt gacccccagc cggttaccaa cagaaccacc ttccttggta     660
gcagaattct cagaagccac cgctgaactg accgtctcat tcacaaacga agtcttcaca     720
actgagactt ctaggagtat caccgccagt ccaaaggagt cagactctcc agctggtcct     780
gcccgccagt actacaccaa gggcaacctg gtccggatat gcctcggggc tgtgatccta     840
```

| | |
|---|---|
| ataatcctgg cggggtttct ggcagaggac tggcacagcc ggaggaagcg cctgcggcac | 900 |
| aggggcaggg ctgtgcagag gccgcttccg ccctgccgc cctcccgct gacccggaaa | 960 |
| tcaaacgggg gtcaggatgg aggccgacag gatgttcaca gccgcgggtt atgttcatga | 1020 |
| ccgctgaacc ccaggcacgg tcgtatccaa gggagggatc atggcatggg aggcgactca | 1080 |
| tgagggcac | 1089 |

<210> SEQ ID NO 4
<211> LENGTH: 951
<212> TYPE: DNA
<213> ORGANISM: Homo sapiens

<400> SEQUENCE: 4

| | |
|---|---|
| atgtctccat ccccgaccgc cctcttctgt cttgggctgt gtctggggcg tgtgccagcg | 60 |
| cagagtggac cgctcccaa gccctccctc caggctctgc ccagctccct ggtgcccctg | 120 |
| gagaagccag tgaccctccg gtgccaggga cctccgggcg tggacctgta ccgcctggag | 180 |
| aagctgagtt ccagcaggta ccaggatcag gcagtcctct tcatcccggc catgaagaga | 240 |
| agtctggctg gacgctaccg ctgctcctac cagaacggaa gcctctggtc cctgcccagc | 300 |
| gaccaggtgg agctcgttgc cacgggagtt tttgccaaac cctcgctctc agcccagccc | 360 |
| ggcccggcgg tgtcgtcagg aggggacgta accctacagt gtcagactcg gtatggcttt | 420 |
| gaccaatttg ctctgtacaa ggaagggac cctgcgccct acaagaatcc cgagagatgg | 480 |
| tacccgggcta gtttccccat catcacggtg accgccgccc acagcggaac ctaccgatgc | 540 |
| tacagcttct ccagcaggga cccatacctg tggtcggccc cagcgacccc ctggagctt | 600 |
| gtggtcacag gaacctctgt gaccccagc cggttaccaa cagaaccacc ttcctcggta | 660 |
| gcagaattct cagaagccac cgctgaactg accgtctcat tcacaaacaa agtcttcaca | 720 |
| actgagactt ctaggagtat caccaccagt ccaaaggagt cagactctcc agctggtcct | 780 |
| gcccgccagt actacaccaa gggcaacctg gtccggatat gcctcggggc tgtgatccta | 840 |
| ataatcctgg cggggtttct ggcagaggac tggcacagcc ggaggaagcg cctgcggcac | 900 |
| aggggcaggg ctgtgcagag gccgcttccg ccctgccgc cctcccgca g | 951 |

<210> SEQ ID NO 5
<211> LENGTH: 20
<212> TYPE: DNA
<213> ORGANISM: Artificial sequence
<220> FEATURE:
<223> OTHER INFORMATION: Taqman primer

<400> SEQUENCE: 5

| | |
|---|---|
| tcccaggaac ctctgtgacc | 20 |

<210> SEQ ID NO 6
<211> LENGTH: 19
<212> TYPE: DNA
<213> ORGANISM: Artificial sequence
<220> FEATURE:
<223> OTHER INFORMATION: Taqman primer

<400> SEQUENCE: 6

| | |
|---|---|
| ctcagaagcc accgctgaa | 19 |

<210> SEQ ID NO 7
<211> LENGTH: 25
<212> TYPE: DNA

```
<213> ORGANISM: Artificial sequence
<220> FEATURE:
<223> OTHER INFORMATION: Taqman primer

<400> SEQUENCE: 7
tttcacactt agcctttgtt tggtt                                         25

<210> SEQ ID NO 8
<211> LENGTH: 15
<212> TYPE: DNA
<213> ORGANISM: Artificial sequence
<220> FEATURE:
<223> OTHER INFORMATION: Taqman primer

<400> SEQUENCE: 8
aagcgcctgc ggcac                                                    15

<210> SEQ ID NO 9
<211> LENGTH: 15
<212> TYPE: DNA
<213> ORGANISM: Artificial sequence
<220> FEATURE:
<223> OTHER INFORMATION: Taqman primer

<400> SEQUENCE: 9
aggaagcgcc tgcgg                                                    15

<210> SEQ ID NO 10
<211> LENGTH: 20
<212> TYPE: DNA
<213> ORGANISM: Artificial sequence
<220> FEATURE:
<223> OTHER INFORMATION: Taqman primer

<400> SEQUENCE: 10
tccttggagc ttgtgtgcaa                                               20

<210> SEQ ID NO 11
<211> LENGTH: 20
<212> TYPE: DNA
<213> ORGANISM: Artificial sequence
<220> FEATURE:
<223> OTHER INFORMATION: Taqman primer

<400> SEQUENCE: 11
ggatccactc aaggctccct                                               20

<210> SEQ ID NO 12
<211> LENGTH: 18
<212> TYPE: DNA
<213> ORGANISM: Artificial sequence
<220> FEATURE:
<223> OTHER INFORMATION: Taqman primer

<400> SEQUENCE: 12
ccggtgtttg cggaatca                                                 18

<210> SEQ ID NO 13
<211> LENGTH: 21
<212> TYPE: DNA
<213> ORGANISM: Artificial sequence
<220> FEATURE:
<223> OTHER INFORMATION: Taqman primer

<400> SEQUENCE: 13
ctcatacgct gtgcaccaga a                                             21
```

<210> SEQ ID NO 14
<211> LENGTH: 21
<212> TYPE: DNA
<213> ORGANISM: Artificial sequence
<220> FEATURE:
<223> OTHER INFORMATION: Taqman primer

<400> SEQUENCE: 14
ctgagcatga aatgcctggt t                                    21

<210> SEQ ID NO 15
<211> LENGTH: 23
<212> TYPE: DNA
<213> ORGANISM: Artificial sequence
<220> FEATURE:
<223> OTHER INFORMATION: Taqman primer

<400> SEQUENCE: 15
ccagctggag agtctgactc ctt                                  23

<210> SEQ ID NO 16
<211> LENGTH: 18
<212> TYPE: DNA
<213> ORGANISM: Artificial sequence
<220> FEATURE:
<223> OTHER INFORMATION: Taqman primer

<400> SEQUENCE: 16
acataacccg cggctgtg                                        18

<210> SEQ ID NO 17
<211> LENGTH: 18
<212> TYPE: DNA
<213> ORGANISM: Artificial sequence
<220> FEATURE:
<223> OTHER INFORMATION: Taqman primer

<400> SEQUENCE: 17
tcccatgcca tgatccct                                        18

<210> SEQ ID NO 18
<211> LENGTH: 23
<212> TYPE: DNA
<213> ORGANISM: Artificial sequence
<220> FEATURE:
<223> OTHER INFORMATION: Taqman primer

<400> SEQUENCE: 18
cggccttcct aattgagact cat                                  23

<210> SEQ ID NO 19
<211> LENGTH: 20
<212> TYPE: DNA
<213> ORGANISM: Artificial sequence
<220> FEATURE:
<223> OTHER INFORMATION: Taqman primer

<400> SEQUENCE: 19
ggagcagcaa gaggaggaga                                      20

<210> SEQ ID NO 20
<211> LENGTH: 19
<212> TYPE: DNA
<213> ORGANISM: Artificial sequence
<220> FEATURE:

```
<223> OTHER INFORMATION: Taqman primer

<400> SEQUENCE: 20
ccggtgagag cagggaaaa                                              19

<210> SEQ ID NO 21
<211> LENGTH: 27
<212> TYPE: DNA
<213> ORGANISM: Artificial sequence
<220> FEATURE:
<223> OTHER INFORMATION: Taqman probe

<400> SEQUENCE: 21
agaaccacct tcctcggtag caggtag                                     27

<210> SEQ ID NO 22
<211> LENGTH: 16
<212> TYPE: DNA
<213> ORGANISM: Artificial sequence
<220> FEATURE:
<223> OTHER INFORMATION: Taqman probe

<400> SEQUENCE: 22
tcacaaacaa agtctt                                                 16

<210> SEQ ID NO 23
<211> LENGTH: 22
<212> TYPE: DNA
<213> ORGANISM: Artificial sequence
<220> FEATURE:
<223> OTHER INFORMATION: Taqman probe

<400> SEQUENCE: 23
ttctaggagt atcaccacca gt                                          22

<210> SEQ ID NO 24
<211> LENGTH: 19
<212> TYPE: DNA
<213> ORGANISM: Artificial sequence
<220> FEATURE:
<223> OTHER INFORMATION: Taqman probe

<400> SEQUENCE: 24
cctcccgcag acccggaaa                                              19

<210> SEQ ID NO 25
<211> LENGTH: 21
<212> TYPE: DNA
<213> ORGANISM: Artificial sequence
<220> FEATURE:
<223> OTHER INFORMATION: Taqman probe

<400> SEQUENCE: 25 ctgaccccg tgtgatttcc g                                            21

<210> SEQ ID NO 26
<211> LENGTH: 14
<212> TYPE: DNA
<213> ORGANISM: Artificial sequence
<220> FEATURE:
<223> OTHER INFORMATION: Taqman probe

<400> SEQUENCE: 26
cgtagccggc tcct                                                   14
```

```
<210> SEQ ID NO 27
<211> LENGTH: 16
<212> TYPE: DNA
<213> ORGANISM: Artificial sequence
<220> FEATURE:
<223> OTHER INFORMATION: Taqman probe

<400> SEQUENCE: 27
cacaggtcct catgcc                                                     16

<210> SEQ ID NO 28
<211> LENGTH: 13
<212> TYPE: DNA
<213> ORGANISM: Artificial sequence
<220> FEATURE:
<223> OTHER INFORMATION: Taqman probe

<400> SEQUENCE: 28
ccgccccggc ccg                                                        13

<210> SEQ ID NO 29
<211> LENGTH: 22
<212> TYPE: DNA
<213> ORGANISM: Artificial sequence
<220> FEATURE:
<223> OTHER INFORMATION: Taqman probe

<400> SEQUENCE: 29
accaccttcc ccggtagcag gt                                              22

<210> SEQ ID NO 30
<211> LENGTH: 14
<212> TYPE: DNA
<213> ORGANISM: Artificial sequence
<220> FEATURE:
<223> OTHER INFORMATION: Taqman probe

<400> SEQUENCE: 30
cacaaacgaa gtct                                                       14

<210> SEQ ID NO 31
<211> LENGTH: 20
<212> TYPE: DNA
<213> ORGANISM: Artificial sequence
<220> FEATURE:
<223> OTHER INFORMATION: Taqman probe

<400> SEQUENCE: 31
ctaggagtat caccgccagt                                                 20

<210> SEQ ID NO 32
<211> LENGTH: 19
<212> TYPE: DNA
<213> ORGANISM: Artificial sequence
<220> FEATURE:
<223> OTHER INFORMATION: Taqman probe

<400> SEQUENCE: 32
cctcccgctg acccggaaa                                                  19

<210> SEQ ID NO 33
<211> LENGTH: 22
<212> TYPE: DNA
<213> ORGANISM: Artificial sequence
<220> FEATURE:
<223> OTHER INFORMATION: Taqman probe
```

```
<400> SEQUENCE: 33
tcctgacccc cgtttgattt cc                                              22

<210> SEQ ID NO 34
<211> LENGTH: 14
<212> TYPE: DNA
<213> ORGANISM: Artificial sequence
<220> FEATURE:
<223> OTHER INFORMATION: Taqman probe

<400> SEQUENCE: 34
ccgtagccag ctcc                                                       14

<210> SEQ ID NO 35
<211> LENGTH: 15
<212> TYPE: DNA
<213> ORGANISM: Artificial sequence
<220> FEATURE:
<223> OTHER INFORMATION: Taqman probe

<400> SEQUENCE: 35
acaggccctc atgcc                                                      15

<210> SEQ ID NO 36
<211> LENGTH: 13
<212> TYPE: DNA
<213> ORGANISM: Artificial sequence
<220> FEATURE:
<223> OTHER INFORMATION: Taqman probe

<400> SEQUENCE: 36
cgccccagcc cgc                                                        13

<210> SEQ ID NO 37
<211> LENGTH: 20
<212> TYPE: DNA
<213> ORGANISM: Artificial sequence
<220> FEATURE:
<223> OTHER INFORMATION: PCR primer

<400> SEQUENCE: 37
ggccatgaag agaagtctgg                                                 20

<210> SEQ ID NO 38
<211> LENGTH: 20
<212> TYPE: DNA
<213> ORGANISM: Artificial sequence
<220> FEATURE:
<223> OTHER INFORMATION: PCR primer

<400> SEQUENCE: 38
agcaagaccc tgtgtccaaa                                                 20

<210> SEQ ID NO 39
<211> LENGTH: 20
<212> TYPE: DNA
<213> ORGANISM: Artificial sequence
<220> FEATURE:
<223> OTHER INFORMATION: PCR primer

<400> SEQUENCE: 39
cagggagttt atgggagcac                                                 20

<210> SEQ ID NO 40
<211> LENGTH: 21
```

<212> TYPE: DNA
<213> ORGANISM: Artificial sequence
<220> FEATURE:
<223> OTHER INFORMATION: PCR primer

<400> SEQUENCE: 40
ccagccatga atacactgga a    21

<210> SEQ ID NO 41
<211> LENGTH: 21
<212> TYPE: DNA
<213> ORGANISM: Artificial sequence
<220> FEATURE:
<223> OTHER INFORMATION: PCR primer

<400> SEQUENCE: 41
aatgtccata aaagcgagtc c    21

<210> SEQ ID NO 42
<211> LENGTH: 20
<212> TYPE: DNA
<213> ORGANISM: Artificial sequence
<220> FEATURE:
<223> OTHER INFORMATION: PCR primer

<400> SEQUENCE: 42
ccgtatttgt gtcctgaacg    20

<210> SEQ ID NO 43
<211> LENGTH: 21
<212> TYPE: DNA
<213> ORGANISM: Artificial sequence
<220> FEATURE:
<223> OTHER INFORMATION: PCR primer

<400> SEQUENCE: 43
aaaaagctcc ccagctctta g    21

<210> SEQ ID NO 44
<211> LENGTH: 21
<212> TYPE: DNA
<213> ORGANISM: Artificial sequence
<220> FEATURE:
<223> OTHER INFORMATION: PCR primer

<400> SEQUENCE: 44
atggccatca ggacctataa a    21

<210> SEQ ID NO 45
<211> LENGTH: 21
<212> TYPE: DNA
<213> ORGANISM: Artificial sequence
<220> FEATURE:
<223> OTHER INFORMATION: PCR primer

<400> SEQUENCE: 45
tatttgttca ggacccacag c    21

<210> SEQ ID NO 46
<211> LENGTH: 21
<212> TYPE: DNA
<213> ORGANISM: Artificial sequence
<220> FEATURE:
<223> OTHER INFORMATION: PCR primer

<400> SEQUENCE: 46

-continued aaggggtccg tgtacctcat a                                                   21

<210> SEQ ID NO 47
<211> LENGTH: 21
<212> TYPE: DNA
<213> ORGANISM: Artificial sequence
<220> FEATURE:
<223> OTHER INFORMATION: PCR primer

<400> SEQUENCE: 47
ctcaaaaggg gaatggagat a                                                   21

<210> SEQ ID NO 48
<211> LENGTH: 21
<212> TYPE: DNA
<213> ORGANISM: Artificial sequence
<220> FEATURE:
<223> OTHER INFORMATION: PCR primer

<400> SEQUENCE: 48
aagagagagc tccgtcctca c                                                   21

<210> SEQ ID NO 49
<211> LENGTH: 20
<212> TYPE: DNA
<213> ORGANISM: Artificial sequence
<220> FEATURE:
<223> OTHER INFORMATION: PCR primer

<400> SEQUENCE: 49
ggagtaggca cagtgacagg                                                     20

<210> SEQ ID NO 50
<211> LENGTH: 21
<212> TYPE: DNA
<213> ORGANISM: Artificial sequence
<220> FEATURE:
<223> OTHER INFORMATION: PCR primer

<400> SEQUENCE: 50
gtttccacag ctgtagcctc t                                                   21

<210> SEQ ID NO 51
<211> LENGTH: 21
<212> TYPE: DNA
<213> ORGANISM: Artificial sequence
<220> FEATURE:
<223> OTHER INFORMATION: PCR primer

<400> SEQUENCE: 51
gagttggctt tggtgaagag a                                                   21

<210> SEQ ID NO 52
<211> LENGTH: 18
<212> TYPE: DNA
<213> ORGANISM: Artificial sequence
<220> FEATURE:
<223> OTHER INFORMATION: PCR primer

<400> SEQUENCE: 52
ctggaggtgg gctctttc                                                       18

<210> SEQ ID NO 53
<211> LENGTH: 20
<212> TYPE: DNA
<213> ORGANISM: Artificial sequence
<220> FEATURE:
<223> OTHER INFORMATION: PCR primer

<400> SEQUENCE: 53
gacgctaccg ctgctcctac                                          20

<210> SEQ ID NO 54
<211> LENGTH: 20
<212> TYPE: DNA
<213> ORGANISM: Artificial sequence
<220> FEATURE:
<223> OTHER INFORMATION: PCR primer

<400> SEQUENCE: 54
tccgatcccc cttcctttac                                          20

<210> SEQ ID NO 55
<211> LENGTH: 17
<212> TYPE: DNA
<213> ORGANISM: Artificial sequence
<220> FEATURE:
<223> OTHER INFORMATION: PCR primer

<400> SEQUENCE: 55
gggaccctgc gccctac                                             17

<210> SEQ ID NO 56
<211> LENGTH: 18
<212> TYPE: DNA
<213> ORGANISM: Artificial sequence
<220> FEATURE:
<223> OTHER INFORMATION: PCR primer

<400> SEQUENCE: 56
ggcggtcacc gtgatgat                                            18

<210> SEQ ID NO 57
<211> LENGTH: 20
<212> TYPE: DNA
<213> ORGANISM: Artificial sequence
<220> FEATURE:
<223> OTHER INFORMATION: PCR primer

<400> SEQUENCE: 57
tcccaggaac ctctgtgacc                                          20

<210> SEQ ID NO 58
<211> LENGTH: 21
<212> TYPE: DNA
<213> ORGANISM: Artificial sequence
<220> FEATURE:
<223> OTHER INFORMATION: PCR primer

<400> SEQUENCE: 58
ctcatacgct gtgcaccaga a                                        21

<210> SEQ ID NO 59
<211> LENGTH: 19
<212> TYPE: DNA
<213> ORGANISM: Artificial sequence
<220> FEATURE:
<223> OTHER INFORMATION: PCR primer

<400> SEQUENCE: 59
ctcagaagcc accgctgaa                                           19

```
<210> SEQ ID NO 60
<211> LENGTH: 21
<212> TYPE: DNA
<213> ORGANISM: Artificial sequence
<220> FEATURE:
<223> OTHER INFORMATION: PCR primer

<400> SEQUENCE: 60
ctgagcatga aatgcctggt t                                              21

<210> SEQ ID NO 61
<211> LENGTH: 25
<212> TYPE: DNA
<213> ORGANISM: Artificial sequence
<220> FEATURE:
<223> OTHER INFORMATION: PCR primer

<400> SEQUENCE: 61
tttcacactt agcctttgtt tggtt                                          25

<210> SEQ ID NO 62
<211> LENGTH: 23
<212> TYPE: DNA
<213> ORGANISM: Artificial sequence
<220> FEATURE:
<223> OTHER INFORMATION: PCR primer

<400> SEQUENCE: 62
ccagctggag agtctgactc ctt                                            23

<210> SEQ ID NO 63
<211> LENGTH: 17
<212> TYPE: DNA
<213> ORGANISM: Artificial sequence
<220> FEATURE:
<223> OTHER INFORMATION: PCR primer

<400> SEQUENCE: 63
tggcacagcc ggaggaa                                                   17

<210> SEQ ID NO 64
<211> LENGTH: 19
<212> TYPE: DNA
<213> ORGANISM: Artificial sequence
<220> FEATURE:
<223> OTHER INFORMATION: PCR primer

<400> SEQUENCE: 64
acatcctgtc ggcctccat                                                 19

<210> SEQ ID NO 65
<211> LENGTH: 15
<212> TYPE: DNA
<213> ORGANISM: Artificial sequence
<220> FEATURE:
<223> OTHER INFORMATION: PCR primer

<400> SEQUENCE: 65
aagcgcctgc ggcac                                                     15

<210> SEQ ID NO 66
<211> LENGTH: 18
<212> TYPE: DNA
<213> ORGANISM: Artificial sequence
<220> FEATURE:
<223> OTHER INFORMATION: PCR primer
```

<400> SEQUENCE: 66
acataacccg cggctgtg					18

<210> SEQ ID NO 67
<211> LENGTH: 15
<212> TYPE: DNA
<213> ORGANISM: Artificial sequence
<220> FEATURE:
<223> OTHER INFORMATION: PCR primer

<400> SEQUENCE: 67
aggaagcgcc tgcgg					15

<210> SEQ ID NO 68
<211> LENGTH: 18
<212> TYPE: DNA
<213> ORGANISM: Artificial sequence
<220> FEATURE:
<223> OTHER INFORMATION: PCR primer

<400> SEQUENCE: 68
tcccatgcca tgatccct					18

<210> SEQ ID NO 69
<211> LENGTH: 13
<212> TYPE: DNA
<213> ORGANISM: Artificial sequence
<220> FEATURE:
<223> OTHER INFORMATION: MGB probe

<400> SEQUENCE: 69
cgaccagctg gag					13

<210> SEQ ID NO 70
<211> LENGTH: 14
<212> TYPE: DNA
<213> ORGANISM: Artificial sequence
<220> FEATURE:
<223> OTHER INFORMATION: MGB probe

<400> SEQUENCE: 70
cgaccaggtg gagc					14

<210> SEQ ID NO 71
<211> LENGTH: 17
<212> TYPE: DNA
<213> ORGANISM: Artificial sequence
<220> FEATURE:
<223> OTHER INFORMATION: MGB probe

<400> SEQUENCE: 71
tagccctgta ccatctc					17

<210> SEQ ID NO 72
<211> LENGTH: 16
<212> TYPE: DNA
<213> ORGANISM: Artificial sequence
<220> FEATURE:
<223> OTHER INFORMATION: MGB probe

<400> SEQUENCE: 72
tagcccggta ccatct					16

<210> SEQ ID NO 73

```
<211> LENGTH: 27
<212> TYPE: DNA
<213> ORGANISM: Artificial sequence
<220> FEATURE:
<223> OTHER INFORMATION: Standard probe

<400> SEQUENCE: 73
agaaccacct tcctcggtag caggtag                                              27

<210> SEQ ID NO 74
<211> LENGTH: 22
<212> TYPE: DNA
<213> ORGANISM: Artificial sequence
<220> FEATURE:
<223> OTHER INFORMATION: Standard probe

<400> SEQUENCE: 74
accaccttcc ccggtagcag gt                                                   22

<210> SEQ ID NO 75
<211> LENGTH: 16
<212> TYPE: DNA
<213> ORGANISM: Artificial sequence
<220> FEATURE:
<223> OTHER INFORMATION: MGB probe

<400> SEQUENCE: 75
tcacaaacaa agtctt                                                          16

<210> SEQ ID NO 76
<211> LENGTH: 14
<212> TYPE: DNA
<213> ORGANISM: Artificial sequence
<220> FEATURE:
<223> OTHER INFORMATION: MGB probe

<400> SEQUENCE: 76
cacaaacgaa gtct                                                            14

<210> SEQ ID NO 77
<211> LENGTH: 22
<212> TYPE: DNA
<213> ORGANISM: Artificial sequence
<220> FEATURE:
<223> OTHER INFORMATION: MGB probe

<400> SEQUENCE: 77
ttctaggagt atcaccacca gt                                                   22

<210> SEQ ID NO 78
<211> LENGTH: 20
<212> TYPE: DNA
<213> ORGANISM: Artificial sequence
<220> FEATURE:
<223> OTHER INFORMATION: MGB probe

<400> SEQUENCE: 78
ctaggagtat caccgccagt                                                      20

<210> SEQ ID NO 79
<211> LENGTH: 14
<212> TYPE: DNA
<213> ORGANISM: Artificial sequence
<220> FEATURE:
<223> OTHER INFORMATION: MGB probe

<400> SEQUENCE: 79
```

-continued

```
ttccgcccct gccg                                                    14

<210> SEQ ID NO 80
<211> LENGTH: 14
<212> TYPE: DNA
<213> ORGANISM: Artificial sequence
<220> FEATURE:
<223> OTHER INFORMATION: MGB probe

<400> SEQUENCE: 80
ttccgcccct cccg                                                    14

<210> SEQ ID NO 81
<211> LENGTH: 19
<212> TYPE: DNA
<213> ORGANISM: Artificial sequence
<220> FEATURE:
<223> OTHER INFORMATION: Standard probe

<400> SEQUENCE: 81
cctcccgcag acccggaaa                                               19

<210> SEQ ID NO 82
<211> LENGTH: 19
<212> TYPE: DNA
<213> ORGANISM: Artificial sequence
<220> FEATURE:
<223> OTHER INFORMATION: Standard probe

<400> SEQUENCE: 82
cctcccgctg acccggaaa                                               19

<210> SEQ ID NO 83
<211> LENGTH: 21
<212> TYPE: DNA
<213> ORGANISM: Artificial sequence
<220> FEATURE:
<223> OTHER INFORMATION: Standard probe

<400> SEQUENCE: 83 ctgaccccccg tgtgatttcc g                                           21

<210> SEQ ID NO 84
<211> LENGTH: 22
<212> TYPE: DNA
<213> ORGANISM: Artificial sequence
<220> FEATURE:
<223> OTHER INFORMATION: Standard probe

<400> SEQUENCE: 84
tcctgacccc cgtttgattt cc                                           22

<210> SEQ ID NO 85
<211> LENGTH: 5
<212> TYPE: PRT
<213> ORGANISM: Homo sapiens

<400> SEQUENCE: 85

Ser Lys Thr Gln His
1               5

<210> SEQ ID NO 86
<211> LENGTH: 5
<212> TYPE: PRT
<213> ORGANISM: Homo sapiens
```

```
<400> SEQUENCE: 86

Pro Glu Ala Leu Asn
1               5

<210> SEQ ID NO 87
<211> LENGTH: 4
<212> TYPE: PRT
<213> ORGANISM: Artificial Sequence
<220> FEATURE:
<223> OTHER INFORMATION: GPRP peptide, inibitor of fibrin
      polymerization.

<400> SEQUENCE: 87

Gly Pro Arg Pro
1

<210> SEQ ID NO 88
<211> LENGTH: 12
<212> TYPE: PRT
<213> ORGANISM: Homo sapiens

<400> SEQUENCE: 88

Arg Pro Leu Pro Pro Leu Pro Pro Leu Pro Gln Thr
1               5                   10

<210> SEQ ID NO 89
<211> LENGTH: 9
<212> TYPE: PRT
<213> ORGANISM: Homo sapiens

<400> SEQUENCE: 89

Pro Leu Pro Pro Leu Pro Pro Leu Pro
1               5

<210> SEQ ID NO 90
<211> LENGTH: 1089
<212> TYPE: DNA
<213> ORGANISM: Homo sapiens

<400> SEQUENCE: 90
gtgccctcat gagtcgcctc ccatgccatg atccctccct tggatacgac cgtgcctggg      60
gttcagcggt catgaacata acccgcggct gtgaacatcc tgtcggcctc catcctgacc     120
cccgtgtgat ttccgggtct gcgggagggg cggcaggggc ggaagcggcc tctgcacagc     180
cctgcccctg tgccgcaggc gcttcctccg gctgtgccag tcctctgcca gaaacccgc      240 caggattatt aggatcacag ccccgaggca tatccggacc aggttgccct tggtgtagta     300
ctggcgggca ggaccagctg gagagtctga ctcctttgga ctggtggtga tactcctaga     360
agtctcagtt gtgaagactt tgtttgtgaa tgagacggtc agttcagcgg tggcttctga     420
gaattctgct accgaggaag gtggttctgt tggtaaccgg ctgggggtca cagaggttcc     480
tgtgaccaca agctccaggg ggtcgctggg ggccgaccac aggtatgggt ccctgctgga     540
gaagctgtag catcggtagg ttccgctgtg gcggcggtc accgtgatga tggggaaact      600
agcccggtac catctctcgg gattcttgta gggcgcaggg tccccttcct tgtacagagc     660
aaattggtca aagccatacc gagtctgaca ctgtagggtt acgtcccctc ctgacgacac     720
cgccgggccg ggctgggctg agagcgaggg tttggcaaaa actcccgtgg caacgagctc     780
cagctggtcg ctgggcaggg accagaggct tccgttctgg taggagcagc ggtagcgtcc     840
agccagactt ctcttcatgg ccgggatgaa gaggactgcc tgatcctggt acctgctgga     900
```

```
actcagcttc tccaggcggt acaggtccac gcccggaggt ccctggcacc ggagggtcac    960
tggcttctcc aggggcacca gggagctggg cagagcctgg agggagggct tggggagcgg   1020
tccactctgc gctggcacac gccccagaca cagcccaaga cagaagaggg cggtcgggga   1080
tggagacat                                                           1089
```